(12) United States Patent
Ivkov

(10) Patent No.: US 7,731,648 B2
(45) Date of Patent: Jun. 8, 2010

(54) MAGNETIC NANOSCALE PARTICLE COMPOSITIONS, AND THERAPEUTIC METHODS RELATED THERETO

(75) Inventor: Robert Ivkov, Marblehead, MA (US)

(73) Assignee: Aduro Biotech, Berkeley, CA (US)

( * ) Notice: Subject to any disclaimer, the term of this patent is extended or adjusted under 35 U.S.C. 154(b) by 1237 days.

(21) Appl. No.: 11/264,680

(22) Filed: Nov. 1, 2005

(65) Prior Publication Data
US 2006/0142749 A1   Jun. 29, 2006
US 2007/0112339 A9   May 17, 2007

Related U.S. Application Data

(63) Continuation-in-part of application No. 10/360,561, filed on Feb. 6, 2003, now abandoned, which is a continuation-in-part of application No. 10/200,082, filed on Jul. 19, 2002, now Pat. No. 6,997,863.

(60) Provisional application No. 60/307,785, filed on Jul. 25, 2001.

(51) Int. Cl.
*A61N 2/00* (2006.01)
(52) U.S. Cl. .......................................... 600/9; 977/904
(58) Field of Classification Search ............... 600/9–15; 607/103, 105; 977/773–777, 904–912, 931; 424/1.29, 1.33, 1.53, 422–423, 426–428, 424/430, 424–437, 489–491, 493–502, 647–648, 424/9.32–9.323
See application file for complete search history.

(56) References Cited

U.S. PATENT DOCUMENTS 4,106,488 A   8/1978   Gordon
4,303,636 A   12/1981  Gordon (Continued)

FOREIGN PATENT DOCUMENTS

DE   10156790   6/2003

(Continued)

OTHER PUBLICATIONS

Denardo et al., Development of Tumor Targeting Bioprobes ($^{111}$In-Chimeric L6 Monoclonal Antibody Nanoparticles) for Alternating Magnetic Field Cancer Therapy, 2005, Clin. Can. Res. 11(19Suppl.): 7087s-7092s.

(Continued)

*Primary Examiner*—John P Lacyk
(74) *Attorney, Agent, or Firm*—Katten Muchin Rosenman LLP

(57) ABSTRACT

Disclosed are thermotherapeutic compositions for treating disease material, and methods of targeted therapy utilizing such compositions. These compositions comprise a) stable single domain magnetic particles; b) magnetic nanoparticles comprising aggregates of superparamagnetic grains; or c) magnetic nanoparticles comprising aggregates of stable single magnetic domain crystals and superparamagnetic grains. These compositions may also comprise a radio isotope, potential radioactive isotope, chemotherapeutic agent. These methods comprise the administration to a patient's body, body part, body fluid, or tissue of bioprobes (energy susceptive materials attached to a target-specific ligand), and the application of energy to the bioprobes so as to destroy, rupture, or inactivate the target in the patient. Energy forms, such as AMF, are utilized to provide the energy. The disclosed methods may be useful in the treatment of a variety of indications, including cancers, diseases of the immune system, central nervous system and vascular system, and pathogen-borne diseases.

103 Claims, 5 Drawing Sheets

U.S. PATENT DOCUMENTS

| | | |
|---|---|---|
| 4,312,364 A | 1/1982 | Convert |
| 4,323,056 A | 4/1982 | Borrelli |
| 4,392,040 A | 7/1983 | Rand |
| 4,452,773 A | 6/1984 | Molday |
| 4,454,234 A | 6/1984 | Czerlinski |
| 4,545,368 A | 10/1985 | Rand |
| RE32,066 E | 1/1986 | Leveen |
| 4,569,836 A | 2/1986 | Gordon |
| 4,574,782 A | 3/1986 | Borrelli |
| 4,590,922 A | 5/1986 | Gordon |
| 4,610,241 A | 9/1986 | Gordon |
| 4,622,952 A | 11/1986 | Gordon |
| 4,662,359 A | 5/1987 | Gordon |
| 4,678,667 A | 7/1987 | Meares |
| 4,708,718 A | 11/1987 | Daniels |
| 4,735,796 A | 4/1988 | Gordon |
| 4,753,894 A | 6/1988 | Frankel |
| 4,758,429 A | 7/1988 | Gordon |
| 4,767,611 A | 8/1988 | Gordon |
| 4,813,399 A | 3/1989 | Gordon |
| 4,889,120 A | 12/1989 | Gordon |
| 4,923,437 A | 5/1990 | Gordon |
| 4,950,221 A | 8/1990 | Gordon |
| 4,979,518 A | 12/1990 | Itoh |
| 4,983,159 A | 1/1991 | Rand |
| 4,996,991 A | 3/1991 | Gordon |
| 5,043,101 A | 8/1991 | Gordon |
| 5,067,952 A | 11/1991 | Gudov et al. |
| 5,087,438 A | 2/1992 | Gordon |
| 5,099,756 A | 3/1992 | Franconi |
| 5,128,147 A | 7/1992 | Leveen |
| 5,169,774 A | 12/1992 | Frankel |
| 5,203,782 A | 4/1993 | Gudov |
| 5,300,750 A | 4/1994 | Carter, Jr. et al. |
| 5,411,730 A | 5/1995 | Kirpotin |
| 5,429,583 A | 7/1995 | Paulus |
| 5,441,746 A | 8/1995 | Chagnon |
| 5,468,210 A | 11/1995 | Matsui |
| 5,506,343 A | 4/1996 | Kufe |
| 5,547,682 A | 8/1996 | Chagnon |
| 5,612,019 A | 3/1997 | Gordon |
| 5,620,480 A | 4/1997 | Rudie |
| 5,622,686 A | 4/1997 | Gordon |
| 5,629,197 A | 5/1997 | Ring |
| 5,658,234 A | 8/1997 | Dunlavy |
| 5,677,171 A | 10/1997 | Hudziak |
| 5,705,157 A | 1/1998 | Greene |
| 5,720,954 A | 2/1998 | Hudziak |
| 5,772,997 A | 6/1998 | Hudziak |
| 5,859,206 A | 1/1999 | Vandlen |
| 5,891,996 A | 4/1999 | Mateo de Acosta del Rio |
| 5,916,539 A | 6/1999 | Pilgrimm |
| 5,922,845 A | 7/1999 | Deo |
| 5,935,866 A | 8/1999 | Chagnon |
| 5,958,374 A | 9/1999 | Meares |
| 5,968,511 A | 10/1999 | Akita |
| 6,008,203 A | 12/1999 | Magnani |
| 6,015,567 A | 1/2000 | Hudziak |
| 6,037,129 A | 3/2000 | Cole |
| 6,054,561 A | 4/2000 | Ring |
| 6,074,337 A | 6/2000 | Tucker |
| 6,149,576 A | 11/2000 | Gray |
| 6,165,440 A | 12/2000 | Esenaliev |
| 6,165,464 A | 12/2000 | Hudziak |
| 6,167,313 A | 12/2000 | Gray |
| 6,190,870 B1 | 2/2001 | Schmitz |
| 6,242,196 B1 | 6/2001 | Spiegelman |
| 6,252,050 B1 | 6/2001 | Ashkenazi |
| 6,281,202 B1 | 8/2001 | Magnani |
| 6,303,755 B1 | 10/2001 | Deo |
| 6,344,203 B1 | 2/2002 | Sandrin |
| 6,347,633 B1 | 2/2002 | Groth |
| 6,387,371 B1 | 5/2002 | Hudziak |
| 6,387,888 B1 | 5/2002 | Mincheff |
| 6,391,026 B1 | 5/2002 | Hung |
| 6,470,220 B1 | 10/2002 | Kraus, Jr. et al. |
| 6,514,481 B1 | 2/2003 | Prasad et al. |
| 6,541,039 B1 | 4/2003 | Lesniak |
| 6,565,887 B1 | 5/2003 | Gray et al. |
| 6,575,893 B2 | 6/2003 | Feucht |
| 6,599,234 B1 | 7/2003 | Gray et al. |
| 6,638,494 B1 | 10/2003 | Pilgrimm |
| 6,669,623 B1 | 12/2003 | Jordan |
| 2001/0011151 A1 | 8/2001 | Feucht |
| 2001/0012912 A1 | 8/2001 | Feucht |
| 2002/0052594 A1 | 5/2002 | Goldenberg |
| 2002/0125975 A1 | 9/2002 | Feucht |
| 2003/0028071 A1 | 2/2003 | Handy et al. |
| 2003/0092029 A1 | 5/2003 | Josephson et al. |
| 2003/0180370 A1 | 9/2003 | Lesniak et al. |
| 2005/0249817 A1 | 11/2005 | Haik et al. |
| 2006/0142749 A1 | 6/2006 | Ivkov |
| 2006/0147380 A1 | 7/2006 | Lanza et al. |

FOREIGN PATENT DOCUMENTS

| | | |
|---|---|---|
| EP | 0040512 | 11/1981 |
| EP | 0136530 | 4/1985 |
| EP | 0333381 A2 | 9/1989 |
| EP | 0400940 A2 | 12/1990 |
| EP | 0543498 A1 | 5/1993 |
| EP | 0913167 | 5/1999 |
| EP | 0673255 B1 | 8/2001 |
| EP | 00344270 B1 | 11/2004 |
| JP | 1244767 | 9/1989 |
| JP | 2004/105722 A | 4/2004 |
| WO | WO 9411023 A1 | 5/1994 |
| WO | WO 97/43005 A1 | 11/1997 |
| WO | WO 99/19000 A1 | 4/1999 |
| WO | WO 00/52714 A1 | 9/2000 |
| WO | WO 01/10500 A1 | 2/2001 |
| WO | WO 01/10501 A1 | 2/2001 |
| WO | WO 01/17611 A1 | 3/2001 |
| WO | WO 01/37721 A2 | 5/2001 |
| WO | WO 03/047633 A2 | 6/2003 |

OTHER PUBLICATIONS

Ivkov et al., Application of High Amplitude Alternating Magnetic Fields for Heat Induction of Nanoparticles Localized in Cancer, 2005, Clin. Can. Res. 11(19Suppl.):7093s-7103s.

Dormann et al., Magnetic Relaxation in Fine-Particle Systems, 1997, from Advances in Chemical Physics, vol. 98, Prigogine et al. eds., John Wiley & Sons, pp. 283-494.

Peasley, Destruction of human immunodeficiency-infected cells by ferrofluid particles manipulated by an external magnetic field: mechanical disruption and selective introduction of cytotoxic or antiretroviral substances into target cells, 1996, Medical Hypotheses, 46: 5-12, No. 1 England (Abstract).

Torchilin et al., Magnetic sephadex as a carrier for enzyme immobilization and drug targeting, 1985, J of Biomedical Materials Res. 19: 461-466, No. 4 United States (Abstract).

Molina et al., Trastuzumab (herceptin), a humanized anti-Her2 receptor monoclonal antibody, inhibits basal and activated Her2 ectodomain cleavage in breast cancer cells, 2001, Cancer Research Jun. 15, 61(12) 4744-4749 (Abstract).

Wong et al., Human scFv antibody fragments specific for the epithelial tumour marker MUC-1, selected by phage display on living cells, 2001, Cancer Immunol. Immunother, April; 50(2): 93-101 (Abstract).

Winthrop et al., Development of a hyperimmune anti-MUC-1 single chain antibody fragment phage display library for targeting breast cancer, 1999, Clin Can Research Oct; 5(10 suppl.): 3088-3094.

Richman et al., Systemic radiotherapy in metastatic breast cancer using 90Y-linked monoclonal MUC-1 antibodies, 2001, Crit Rev Oncol Hematol 38: 25-35, Ireland (Abstract).

Kobayashi et al., Targeting hyperthermia for renal cell carcinoma using human MN antigen-specific magnetoliposomes, 2001, Japanese J. of Cancer Res. 92: No. 10 (Abstract).

Young et al., A pulsed power supply system for producing high intensity magnetic and electric fields for medical applications, IEEE Conference Record-Abstracts, PPPS-2001 Pulsed Power Plasma Science 2001, 28th IEEE International Conference on Plasma Science and 13th IEEE International Pulsed Power Conference (Cat. No. 01CH37255) 2001, pp. 322, USA (Abstract).

Peterson et al.., Effect of multiple, repeated doses of radioimmunotherapy on target antigen expression (breast MUC-1 mucin in breast carcinomas, 1997, Cancer Res. 57(6): 1103-1108 (Abstract).

Diaz et al., Expression of epithelial mucins Muc1, Muc2, and Muc3 in ductal carcinoma in situ of the breast, 2001, Breast J. 7(1): 40-45 (Abstract).

Barratt-Boyles, Making the most of mucin: a novel target for tumor immunotherapy, 1996, Cancer Immunol. Immunother. 43(3): 142-151.

Menard et al., Role of Her2 gene overexpression in breast carcinoma, 2000, J. Cell Physiol. 182(2): 150-162 (Abstract).

Hadden, The immunology and immunotherapy of breast cancer: an update, 1999, Int. J. Immunopharacol., 21(2): 79-101 (Abstract).

Tucker et al., Defining the heating characteristics of ferromagnetic implants using calorimetry, 2000, J. of Biomedical Materials Research 53: 791-798 (Abstract).

Takegami et al., New ferromagnetic bone cement for local hyperthermia, 1998, J. Biomedical Materials Research 43: 210-214 (Abstract).

Paulus et al., Corrosion analysis of NiCu and PdCo thermal seed alloys used as interstitial hyperthermia implants, 1997, vol. 18: 1609-1614 (Abstract).

Graef, Materials for low Curie termperature induction hearing of tumors (Hyperthermia), 1991, Ph.D. Dissertation, University of Arizona (Abstract).

Petrarca et al., Isolation of MUCI-primed B lymphocytes from tumour-draining lymph nodes by immonomagnetic beads, 1999, Cancer Immunology Immunotherapy 47 No. 5: 272-277 (Abstract).

Shinkai et al., Targeting hyperthermia for renal cell carcinoma using human mn antigen-specific magnetoliposomes, 2001, Jpn J. Cancer Res. 92: 1138-1145 (Abstract).

Suzuki et al., Preparation and characteristics of magnetite-labelled antibody with the use of poly(ethylene glycol) derivatives, 1995, Biotechnol Appl Biochem, 21: 335-345.

Shinkai et al., Antibody-conjugated magnetoliposomes for targeting cancer cells and their application in hyperthermia, 1994, Biotechnol Appl Biochem 21: 125-137.

Jordan et al., Magnetic fluid hyperthermia (MFH): Cancer treatment with AC magnetic field induced excitation of biocompatible superparamagnetic nanoparticles, 1999, J. Magnetism and Magnetic Materials, 201: 413-419.

Jordan et al., Inductive heating of ferromagnetic particles and magnetic fluids: physical evaluation of their potential for hyperthermia, 1993, Int. J. Hyperthermia 9: 51-68.

Jordan et al., Magnetic Fluid Hyperthermia (MFH) in Scientific and Clinical Applications of Magnetic Carriers, Hafeli et al., ed, 1997, 569-595 USA.

Chan et al., Synthesis and evaluation of colloidal magnetic iron oxides for the site-specific radiofrequency-induced hyperthermia of cancer, 1993, J. Magnetism and Magnetic Materials, 122: 374-378, Holland.

Brusentsov et al., Evaluation of ferromagnetic fluids and suspensions for the site-specific radiofrequency-induced hyperthermia of MXII sarcoma cells in vitro, 2001, J. Magnetism and Magnetic Materials, 225: 113-117.

Jones et al., Experimental examination of a targeted hyperthermia system using inductively heated ferromagnetic microspheres in rabbit kidney, 2001, Physics in Medicine and Biology 46: 385-398.

Jones et al., Evaluation of ferromagnetic materials for low-frequency hysteresis heating of tumors, 1992, Physics in Medicine and Biology 37: 293-299.

Moroz et al., Targeting liver tumors with hyperthermia: Ferromagnetic embolization in a rabbit liver tumor model, 2001, J. of Surgical Oncology 78: 22-29.

Hiergeist et al., Application of magnetic ferrofluids for hyperthermia, 1999, J. Magnetism and Magnetic Materials 201: 420-422.

Shinkai et al., Intracellular hyperthermia for cancer using magnetite cationic liposomes: In vitro study, Jpn, 1996, J. Cancer Research 87: 1179-1183.

Carter, Improving the efficacy of antibody-based cancer therapies, 2001, Nature Reviews 1: 118-129.

McDevitt et al., Tumor Therapy with targeted atomic nanogenerators, 2001, Science, 294: 1537-1550.

Segal et al., Introduction: bispecific antibodies, 2001, J. Immunol. Methods, 248: 1-6.

Reiter et al., Recombinant immunotoxins in targeted cancer cell therapy, 2001, Adv. Can. Res. pp. 93-124.

Hergt et al., Physical limits of hyperthermia using magnetite fine particles, 1998, IEEE Trans. On Mag., 34: 3745-3754.

Hynynen et al., State of the art in medicine: Hyperthermia in cancer treatment, 1990, Investigative Radiology, 2: 824-834.

Jordan et al.., Cellular uptake of magnetic fluid particles and their effects on human adenocarcinoma cells exposed to AC magnetic fields in vitro, 1996, Int. J. Hyperthermia 12: 705-722.

Chan et al.., Physical chemistry and in vivo tissue heating properties of colloidal magnetic iron oxides with increased power adsorption rates in Scientific and Clinical Applications of Magnetic Carriers, Hafeli et al. eds., 1997, pp. 607-618, Plenum Press, New York, USA.

Suzuki et al.., Studies on liposomal ferromagnetic particles and a technique of high frequency inductive heating, Jpn, 1990, J. Soc. Cancer Ther., 25: 2649-2658.

Gordon et al., Intracellular hyperthermia: a biophysical approach to cancer treatment via intracellular temperature and biophysical alterations, 1979, Medical Hypothesis 5: 83-102.

Goldin et al.., The effects of diapulse on the healing of wounds: a double-blind randomized controlled trial in man, 1981, Brit. J. of Plastic Surgery 34: 267-270.

Gilchrist et al., Selective inductive heating of lymph nodes, 1957, Annals of Surgery 146: 596-606.

Luderer et al., Glass-ceramic-mediated, magnetic-field-induced localized hyperthermia: Response of a murine mammary carcinoma, 1983, Radiation Research 94: 190-198.

Bartlett et al., On the use of ferromagnetic microparticles in microwave and radio frequency hyperthermia, 1988, J. of the Inst. of Electronic and Radio Engineers 58: 197-201.

Bacri et al., Use of magnetic nanoparticles for thermolysis of cells in a ferrofluid, 1997, Scientific and Clinical Applications of Magnetic Carriers, Hafeli et al., eds., pp. 597-606, Plenum Press, New York, USA.

Mitsumori et al., Targeted hyperthermia using dextran magnetite complex: A new treatment modality for liver tumors, 1996, Hepato-Gastroenterology, 43: 1431-1437.

Borelli et al.., Hysteresis heating for the treatment of tumours, 1984, Phys Med Biol. 29 No. 5: 487-494, England.

Mitsumori et al., Development of intra-arterial hyperthermia using a dextran-magnetite complex, 1994, Int. J. Hyperthermia 10: 785-793.

Csuka et al., Prognostic factors of breast cancer, 2000, Magy. Onkol 44: 53-60 (Abstract).

Luftner et al., Nuclear matrix proteins as biomarkers for breast cancer, 2002, Expert Rev. Mol. Diag. 2:23-31 (Abstract).

Krishnamurthy et al., Molecular and biologic markers of premalignant lesions of human breast, 2002, Adv. Anat. Pathol. 9: 185-197 (Abstract).

Palmu et al., Expression of C-KIT and HER-2 tyrosine kinase receptors in poor-prognosis breast cancer, 2002, Anticancer Res. 22: 411-414 (Abstract).

Esteva et al., Expression of erbB/HER receptors, heregulin and P38 in primary breast cancer using quantitative immunohistochemistry, 2002, Pathol. Oncol. Res. 7: 171-177 (Abstract).

O'Hanlon et al., An immunohistochemical study of p21 and p53 expression in primary node-positive breast carcinoma, 2002, Eur. J. Surg. Oncol. 28: 103-107 (Abstract).

Aguilar et al., The transmembrane heregulin precursor is functionally active, 2001, J. Biol. Chem. 276: 44099-44107 (Abstract).

Defazio et al., Expression of c-erbB receptors, heregulin and estrogen receptor in human breast cell lines, 2000, Int. J. Cancer 87: 487-498 (Abstract).

Hadden, The immunology and immunotherapy of breast cancer: an update, 1999, Int. J. Immunopharmacol. 21: 79-101 (Abstract).

Gion et al., CA27.29: a valuable marker for breast cancer management. A confirmatory multicentric study on 603 cases, 2001, Eur. J. Cancer 37: 355-363 (Abstract).

Suo et al., EGFR family expression in breast carcinomas. c-erbB-2 and c-erbB-4 receptors have different effects on survival, 2002, J. Pathol. 196: 17-25 (Abstract).

Parker et al., E-cadherin as a prognostic indicator in primary breast cancer, Br. J. Cancer 85: 1958-1963 (Abstract).

Lakhani et al., The pathology of familial breast cancer: predictive value of immunohistochemical markers estrogen receptor, progesterone receptor, HER-2, and p53 in patients with mutations in BRCA1 and BRCA2, 2002, J. Clin. Oncol. 20: 2310-2318 (Abstract).

Moritani et al., Availability of CD10 immunohistochemistry as a marker of breast myoepithelial cells on paraffin sections, 2002, Mod. Pathol. 15: 397-405 (Abstract).

Spizzo et al., Prognostic significance of Ep-CAM and Her-2/neu overexpression in invasive breast cancer, 2002, Int. J. Cancer 98: 883-888 (Abstract).

Vanpoznak et al., Assessment of molecular markers of clinical sensitivity to single-agent taxane therapy for metastatic breast cancer, J.Clin. Oncol. 20: 2319-2326 (Abstract).

Oppezzo et al., Production and functional characterization of two mouse/human chimeric antibodies with specificity for the tumor associated Tn antigen, 2000, Hibridoma 19: 229-239 (Abstract).

Babino et al., Tn antigen is a pre-cancerous biomarker in breast tissue and serum in n-nitrosomethylurea-induced rat carcinogenesis, 2000, Int. J. Cancer 86: 753-759 (Abstract).

Lapetti et al., Controlling tumor-derived and vascular endothelial cell growth: role of the 4Ff2 cell surface antigen, 2001, Am. J. Pahol., 159: 165-178 (Abstract).

Molina et al., Trastuzumab (herceptin), a humanized anti-Her2 receptor monoclonal antibody, inhibits basal and activated Her2 ectodomain cleavage in breast cancer cells, 2001, Cancer Res. 61: 4744-4749 (Abstract).

Wong et al., Human scFv antibody fragments specific for the epithelial tumor marker MUC-1, selected by phage display on living cells, 2001, Cancel Immunol. Immunother. 50::93-101 (Abstract).

Isaacs et al., Humanized monoclonal antibody therapy for rheumatoid arthritis, 1992, Lancet 240:748-752 (Abstract).

Isaacs et al., Humanized anti-CD4 monoclonal antibody therapy of autoimmune and inflammatory disease, 1997, Clin. Exp. Immunol, 110: 158-166 (Abstract).

Coles et al., Pulsed monoclonal antibody treatment and autoimmune thyroid disease in multiple sclerosis, 1999, Lancet 354: 1691-1695 (Abstract).

Moseley et al., HMFGI antigen: a new marker for carcinomatous meningitis, 1989, Int. J. Cancer 44: 440-444 (Abstract).

Stockhammer et al., Vascular endothelial growth factor in CSF: a biological marker for carcinomatous meningitis, 2000, Neurology: 54: 1670-1676 (Abstract).

Gourevitch et al., Polymorphic epithelial mucin (MUC-1)-containing circulating immune complexes in carcinoma patients, 1995, Br. J. Cancer 72: 934-938 (Abstract).

Ramakrishna et al., Generation and phenotypic characterization of new human ovarian cancer cell lines with the identification of antigens potentially recognizable by HLA-restricted cytotoxic T cells, 1997, Int. J. Cancer 73: 143-150 (Abstract).

Snijdewint et al., Cellular and humoral immune responses to MUC1 mucin tandem-repeat peptides in ovarian cancer patients and controls, 1999, Cancer Immunol. Immunother. 48: 47-55 (Abstract).

Wu et al., Activated matrix metalloproteinase-2-a potential marker of prognosis for epithelial ovarian cancer, 2002, Gynecol. Oncol 84: 126-134 (Abstract).

Taylor et al., Shed membrane fragment-associated markers for endometrial and ovarian cancers, 2002, Gynecol. Oncol. 84: 443-448 (Abstract).

Davidson et al., Ovarian carcinoma and serous effusions. Changing views regarding tumor progression and review of current literature, 2001, Anal. Cell Pathol. 23: 107-128 (Abstract).

Jiang et al., Vaccination with a mixed vaccine of autogenous and allogenic breast cancer cells and tumor associated antigens CA15-3, CEA and CA125-results in immune and clinical responses in breast cancer patients, 2000, Cancer Biother Radiopharm 15: 495-505 (Abstract).

Garcia-Pachon et al., Diagnostic value of C-reactive protein in exudative pleural effusions, 2002, Eur. J. Intern. Med. 13: 246-249 (Abstract).

Ma et al., Molecular cloning and expression analysis of feline melanoma antigen (MAGE) obtained from a lymphoma cell line, 2001, Vet. Immunol. Immunopathol. 83: 241-252 (Abstract).

Barker et al., The MAGE proteins: emerging roles in cell cycle progression, apoptosis, and neurogenic disease, 2002, J. Neurosci. Res. 67: 705-712 (Abstract).

McTernan et al., Increased resistin gene and protein expression in human abdominal adipose tissue, 2002, J. Clin. Endocrinol. Metab. 87: 2407 (Abstract).

Xu et al., Altered tumor necrosis factor-alpha (TNF-alpha) processing in adipocytes and increased expression of transmembrane TNF-alpha in obesity, 2002, Diabetes 51: 1876-1883 (Abstract).

George et al., Functional inhibition of Ras by S-trans, trans-farnesyl thiosalicylic acid attenuates atherosclerosis in apolipoprotein E knockout mice, 2002, Circulation 105: 2416-2422 (Abstract).

Ibrahimi et al., Role of CD36 in membrane transport of long-chain fatty acids, 2002, Curr. Opin. Clin. Nutr. Metab. Care 5: 139-145 (Abstract).

Miyawaki et al., Inhibition of gastric inhibitory polypedtide signaling prevents obesity, 2002, Nat. Med. 8: 738-742 (Abstract).

Babincova, Superparamagnetic gel as a novel material for electromagnetically induced hyperthermia, J. of Magnetism and Magnetic Materials 225 (2001) 109-112.

International Search Report for PCT/US02/23650.

Dormann et al., Magnetic Relaxation in Fine-Particle Systems, in *Advances in Chemical Physics*, vol. XCVIII, edited by 1. Prigogine and Stuart A Rice; Year: 1997 Publisher: John Wiley & Sons, Inc.

Ivkov et al., "Application of high amplitude alternating magnetic fields for heat induction of nanoparticles localized in cancer", 2005, Clinical Cancer Research, vol. 11(19 Suppl), pp. 7093s-7103s.

Denardo et al., "Development of tumor targeting bioprobes (111In-Chimeric L6 monoclonal antibody nanoparticles) for alternating magnetic field cancer therapy", 2005, Clinical Cancer Research, vol. 11(19 Suppl), pp. 7087s-7092s.

Gruttner et al., Synthesis and Antibody Conjugation of Magnetic Nanoparticles with Improved Specific Power Absorption Rates for Alternating Magnetic Field Cancer Therapy, 2007, J. Magnetism and Magnetic Materials 311:181-186 (Dec. 13, 2006-available online).

MAGNETIC NANOSCALE PARTICLE COMPOSITIONS, AND THERAPEUTIC METHODS RELATED THERETO

CROSS REFERENCE TO RELATED APPLICATIONS

This is a Continuation-in-Part application claiming the benefit of and priority to Non-Provisional application Ser. No. 10/200,082 filed on Jul. 19, 2002, now U.S. Pat. No. 6,997,863, which is incorporated hereby reference, and a Continuation-in Part of Non-Provisional Application Ser. No. 10/360,561 filed on Feb. 6, 2003, now abandoned, and Provisional Patent Application Ser. No. 60/307,785 filed on Jul. 25, 2001, which is incorporated herein by reference.

TECHNICAL FIELD

The present invention relates generally to targeted magnetic nanotherapy compositions and methods, and specifically, to magnetic nanoscale particle compositions that comprise an energy susceptive material that is attached to a target-specific ligand, and therapeutic methods that comprise the administration of such compositions to a patient's body, body part, tissue, or body fluid, and the administration of energy from an energy source, so as to destroy or inactivate the target.

BACKGROUND

The time between the onset of disease in a patient and the conclusion of a successful course of therapy is often unacceptably long. Many diseases remain asymptomatic and evade detection while progressing to advanced, and often terminal, stages. In addition, this period may be marked by significant psychological and physical trauma for the patient due to the unpleasant side effects of even correctly prescribed treatments. Even diseases that are detected early may be most effectively treated only by therapies that disrupt the normal functions of healthy tissue or have other unwanted side effects.

One such disease is cancer. Despite considerable research effort and some success, cancer is still the second leading cause of death in the United States, claiming more than 500,000 lives each year according to American Cancer Society estimates. Traditional treatments are invasive and/or are attended by harmful side effects (e.g., toxicity to healthy cells), often making for a traumatic course of therapy with only modest success. Early detection, a result of better diagnostic practices and technology, has improved the prognosis for many patients. However, the suffering that many patients must endure makes for a more stressful course of therapy and may complicate patient compliance with prescribed therapies. Further, some cancers defy currently available treatment options, despite improvements in disease detection. Of the many forms of cancer that still pose a medical challenge, prostate, breast, lung, and liver claim the vast majority of lives each year. Colorectal cancer, ovarian cancer, gastric cancer, leukemia, lymphoma, melanoma, and their metastases may also be life threatening.

Conventional treatments for breast cancer, for example, typically include surgery followed by radiation and/or chemotherapy. These techniques are not always effective, and even if effective, they suffer from certain deficiencies. Surgical procedures range from removal of only the tumor (lumpectomy) to complete removal of the breast. In early stage cancer, complete removal of the breast may provide an assurance against recurrence, but is disfiguring and requires the patient to make a very difficult choice. Lumpectomy is less disfiguring, but can be associated with a greater risk of cancer recurrence. Radiation therapy and chemotherapy are arduous and are not completely effective against recurrence.

Treatment of pathogen-based diseases is also not without complications. Patients presenting symptoms of systemic infection are often mistakenly treated with broad-spectrum antibiotics as a first step. This course of action is completely ineffective when the invading organism is viral. Even if a bacterium (e.g., $E.\ coli$) is the culprit, the antibiotic therapy eliminates not only the offending bacteria, but also benign intestinal flora in the gut that are necessary for proper digestion of food. Hence, patients treated in this manner often experience gastrointestinal distress until the benign bacteria can repopulate. In other instances, antibiotic-resistant bacteria may not respond to antibiotic treatment. Therapies for viral diseases often target only the invading viruses themselves. However, the cells that the viruses have invaded and "hijacked" for use in making additional copies of the virus remain viable. Hence, progression of the disease is delayed, rather than halted.

For these reasons, it was desirable to provide improved and alternative techniques for treating disease, particularly techniques that are less invasive and traumatic to the patient than the existing techniques, and effective only locally at targeted sites, such as diseased tissue, pathogens, or other undesirable matter in the body. It was also desirable to provide techniques capable of being performed in a single or very few treatment sessions (minimizing patient non-compliance), with minimal toxicity to the patient, and which could be targeted to the diseased tissues without requiring significant operator skill and input.

One such alternative technique is immunotherapy, which is a rapidly expanding type of therapy used for treating a variety of human diseases including cancer, for example. The FDA has approved a number of antibody-based cancer therapeutics. The ability to engineer antibodies, antibody fragments, and peptides with altered properties (e.g., antigen binding affinity, molecular architecture, specificity, valence, etc.) has enhanced their use in therapies. Cancer immunotherapeutics have made use of advances in the chimerization and humanization of murine antibodies to reduce immunogenic responses in humans. High affinity human antibodies have also been obtained from transgenic animals that contain many human immunoglobulin genes. In addition, phage display technology, ribosome display, and DNA shuffling have allowed for the discovery of antibody fragments and peptides with high affinity and low immunogenicity for use as targeting ligands. All of these advances have made it possible to design an immunotherapy that has a desired antigen binding affinity and specificity, and minimal immune response.

The field of cancer immunotherapy makes use of markers that are over-expressed by cancer cells (relative to normal cells) or expressed only by cancer cells. The identification of such markers is ongoing and the choice of a ligand/marker combination is critical to the success of any immunotherapy. Immunotherapeutics fall into at least three classes: (1) deployment of antibodies that, themselves, target growth receptors, disrupt cytokine pathways, or induce complement or antibody-dependent cytotoxicity; (2) direct arming of antibodies with a toxin, a radionuclide, or a cytokine; (3) indirect arming of antibodies by attaching them to immunoliposomes used to deliver a toxin or by attaching them to an immunological cell effector (bispecific antibodies). Although armed antibodies have shown potent tumor activity in clinical trials, they have also exhibited unacceptably high levels of toxicity to patients.

The disadvantage of therapies that rely on delivery of immunotoxins or radionuclides (i.e., direct and indirect arming) has been that, once administered to the patient, these agents are active at all times. These therapies often cause damage to non-tumor cells and present toxicity issues and delivery challenges. For example, cancer cells commonly shed surface-expressed antigens (targeted by immunotherapeutics) into the blood stream. Immune complexes can be formed between the immunotherapeutic and the shed antigen. As a result, many antibody-based therapies are diluted due to the interaction of the antibody with these shed antigens rather than interacting with the cancer cells, and thereby reducing the true delivered dose. Thus, a "therapy-on-demand" approach that minimizes adverse side effects and improves efficacy would be preferable.

With thermotherapy, temperatures in a range from about 40° C. to about 46° C. (hyperthermia) can cause irreversible damage to disease cells. However, healthy cells are capable of surviving exposure to temperatures up to around 46.5° C. Elevating the temperature of individual cells in diseased tissue to a lethal level (cellular thermotherapy) may provide a superior treatment option. Pathogens implicated in disease and other undesirable matter in the body can also be destroyed via exposure to locally high temperatures.

Temperatures greater than 46° C. may also be effective for the treatment of cancer and other diseases by causing an instantaneous thermo-ablative response. However, accurate and precise targeting is necessary to ensure that a minimal amount of healthy tissue is exposed to such temperatures. Failure to achieve such a level of targeting may produce increased detrimental side effects, and thereby reducing the benefits of the treatment.

Hyperthermia may hold promise as a treatment for cancer and other diseases because it induces instantaneous necrosis (typically referred to as "thermo-ablation") and/or a heat-shock response in cells (classical hyperthermia), leading to cell death via a series of biochemical changes within the cell. State-of-the-art systems that employ microwave or radio frequency (RF) hyperthermia, such as annular phased array systems (APAS), attempt to tune energy for regional heating of deep-seated tumors. Such techniques are limited by the heterogeneities of tissue electrical conductivities and that of highly perfused tissue. This leads to the as-yet-unsolved problems of "hot spot" phenomena in untargeted tissue with concomitant under-dosage in the desired areas. The result is often a lower than expected therapeutic ratio, and an inherent difficulty to determine with adequate precision the heat dose delivered to the desired area. The latter precludes the development of prescriptive clinical protocols, which are necessary to ensure reproducible and predictable patient benefits following treatment. All of these factors make selective heating of specific regions with such systems very difficult.

Another strategy that utilizes RF hyperthermia requires surgical implantation of microwave or RF based antennae or self-regulating thermal seeds. While this approach avoids problems related to dose determination and some of the problems associated with targeting, it requires an invasive procedure to implant the thermal seeds. In addition to its invasiveness, this approach provides few (if any) options for treatment of metastases because it requires knowledge of the precise location of the primary tumor. The seed implantation strategy is thus incapable of targeting undetected individual cancer cells or cell clusters not immediately adjacent to the primary tumor site. Clinical success of this strategy is hampered by problems with the targeted generation of heat at the desired tumor tissues.

A strategy for treating a disease by generating heat within a tumor using superparamagnetic particles (having characteristic relaxation time$\approx 10^{-9}$ sec) that are suspended in a suitable medium, referred to as magnetic fluids, and exposing the patient to an alternating magnetic field (AMF) has been proposed (see e.g., U.S. Pat. No. 6,541,039 to Lesniak et al. and U.S. Pat. No. 6,470,220 to Kraus, et al.). While some variations exist, generally the methods disclosed in the prior art involve the introduction of the magnetic fluid directly into the region to be treated and heating the particles by exposing a significant portion of the patient to low amplitude (less than 16 kA/m) alternating magnetic fields with frequency of between 50 kHz and 200 kHz, including the region of interest. It is well established that exposing a significant portion of a patient to an AMF will increase tissue temperature over the whole region exposed, and even the core body temperature, significantly because of the eddy currents generated by the interaction of the AMF with tissues. Indeed, this is the general strategy used with antennae-based or annular phased array RF devices described above. A cancer tumor located within this region would thus experience an elevated temperature even without a magnetic fluid. Tumor temperature increases to a range of about 40° C. to 43° C. are reported in some cases. Such tumor temperatures seem low when one considers the relatively large amounts, about 10 mg to 100 mg particles per gram of tumor, of superparamagnetic particles injected directly into the tumor. This suggests that a significant portion of the heat is the result of direct AMF effects on tissue (eddy current), with a lesser degree of heat contributed by the presence of the particles.

The magnetic fluids as described comprise non-interacting superparamagnetic particles, which are stated to be preferred because of their decreased tendency to aggregate. Because the magnetic particles comprising the fluid are superparamagnetic, viscous heating is the mechanism giving rise to particle rotation that deposits energy into the medium due to its viscosity, i.e., Brownian relaxation. As disclosed in the prior art, superparamagnetic particles are preferred because they will have zero, or near zero, remanence, and thus a reduced tendency to aggregate, which occurs when their magnetic moments are non-interacting. Heating via Neél relaxation (magnetic hysteresis) is precluded in this instance, unless the AMF period is significantly shorter (less than $10^{-9}$ sec) than the characteristic relaxation time of the particle magnetic moments. Thus, magnetic hysteresis heating with an AMF is only possible if the AMF frequency is greater than 1 GHz. For methods involving the compositions of the magnetic (superparamagnetic) fluids described, and the typical AMF frequencies disclosed therein (about 100 kHz), there is no possible contribution of heating via Neél relaxation.

SUMMARY OF THE INVENTION

Hyperthermia for treatment of disease using magnetic fluids exposed to RF fields has been recognized for several decades. However, a major problem with magnetic fluid hyperthermia has been the inability to selectively deliver a lethal dose of particles to the cells or pathogens of interest, particularly when the composition is limited to particles possessing characteristic relaxation times much shorter than the period of the applied RF.

The biology of heat damage to cells is well understood, as is the clinical potential that a suitably targeted heating approach holds for the treatment of disease. This results from either the cytotoxic effect of heat, or the enhanced cytotoxic effect of radiation or chemotherapy resulting from heat sensitization of the cell when heat is combined with these treatments, or it can a combination of these. Heat applied to a cell in combination with ionizing radiation, such as ultraviolet, x-ray, gamma, beta, alpha, neutron, etc., or chemotherapy often results in an enhanced cytotoxic effect that may be significantly greater than expected from an additive combination of the ionizing energy or chemotherapy doses. Often, a cell will exhibit a high level of susceptibility to an otherwise sub-lethal dose of either chemotherapeutic agent or ionizing radiation when that dose is combined with heat, also at sub-lethal dose, in some combination. Such a combination therapy has a demonstrable significant clinical potential because damaging side effects from a dose of either heat or ionizing radiation may be avoided. Suitably targeting the combined form of treatment, i.e., in the bioprobes, thus has significant advantages over untargeted applications of either treatment modality or their combination.

In view of the above, there is a need for thermotherapeutic compositions for treating diseased tissue, pathogens, or other undesirable matter, that comprise a) stable single domain magnetic particles (characteristic relaxation time greater than $10^9$ sec); b) magnetic nanoparticles comprising aggregates of superparamagnetic grains where the interacting magnetic moments create a collective state possessing characteristic relaxation times that are matched to the period of magnetic fields applied to a target within a patient's body; or c) magnetic nanoparticles comprising aggregates of stable single magnetic domain crystals and superparamagnetic grains, where the interactions of the stable single domain and superparamagnetic magnetic moments result in a collective state that increases the superparamagnetic characteristic relaxation time to a value much greater than $10^9$ sec. It is also desirable to have hyperthermia-based treatment methods that incorporate selective delivery of such thermotherapeutic compositions, and that are safe and effective, short in duration, and require minimal invasion.

It is, therefore, an object of the present invention to provide a thermotherapeutic magnetic composition for treating disease material that comprises a) stable single domain magnetic particles (characteristic relaxation time greater than $10^9$ sec); b) magnetic nanoparticles comprising aggregates of superparamagnetic grains where the interacting magnetic moments create a collective state possessing characteristic relaxation times that are matched to the period of magnetic fields applied to a target within a patient's body; or c) magnetic nanoparticles comprising aggregates of stable single magnetic domain crystals and superparamagnetic grains, where the interactions of the stable single domain and superparamagnetic magnetic moments result in a collective state that increases the superparamagnetic characteristic relaxation time to a value much greater than $10^9$ sec.

It is another object of the present invention to provide a method for treating disease material, that comprises selective delivery of such thermotherapeutic compositions, and that are safe and effective, short in duration, and require minimal invasion.

It is another object of the present invention to provide a treatment method that involves the administration of a magnetic material composition, that comprises stable single domain magnetic grains, or aggregates of magnetically coupled superparamagnetic grains, with characteristic relaxation time of the collective magnetic state appropriately tuned for heating via magnetic hysteresis losses, or aggregates of magnetically coupled stable single domain and superparamagnetic grains, attached to a target-specific ligand, to a patient, and the application of an alternating magnetic field to inductively heat the magnetic material composition via magnetic hysteresis losses, e.g., Neél relaxation.

It is another object of the present invention to provide such a treatment method that comprises the detection of at least one location of accumulation of the magnetic material composition within the patient's body prior to the application of an alternating magnetic field.

It is another object of the present invention to provide such a treatment method that comprises the application of the alternating magnetic field when the magnetic material composition is outside of the patient's body.

It is another object of the present invention to provide a treatment method that involves the induction of a desired pathological effect by inductively heating the magnetic material to cause necrosis, apoptosis, or deactivation of disease material.

It is another object of the present invention to provide a composition and a treatment method that combine the benefits of hyperthermia, radiation, chemotherapy within the nanoparticle composition.

It is yet another object of the present invention to provide a method for administration of a magnetic material composition, which may be intraperitoneal injection, intravascular injection, intramuscular injection, subcutaneous injection, topical, inhalation, ingestion, rectal insertion, wash, lavage, rinse, or extracorporeal administration into a patient's bodily materials.

It is a further object of the present invention to provide methods for the treatment of tissue in a safe and effective manner, with minimal invasion, and short treatment periods.

The present invention pertains to thermotherapeutic magnetic compositions for treating disease material. In one embodiment, the composition comprises single-domain magnetic particles (characteristic relaxation time greater than $10^9$ sec) attached to a target-specific ligand. In another embodiment, the composition comprises magnetic nanoparticles comprising aggregates of superparamagnetic grains, where the interacting magnetic moments create a collective state possessing characteristic relaxation times that are matched to the period of magnetic fields applied to a target within a patient's body. In another embodiment, the composition comprises magnetic nanoparticles comprising aggregates of stable single magnetic domain crystals and superparamagnetic grains, where the interactions of the stable single domain and superparamagnetic magnetic moments result in a collective state that increases the superparamagnetic characteristic relaxation time to a value much greater than $10^{-9}$ sec.

The present invention pertains to methods for treating diseased tissue, pathogens, or other undesirable matter in a patient. In one embodiment, the treatment method comprises the administration of a thermotherapeutic magnetic composition that comprises single-domain magnetic particles attached to a target-specific ligand, to a patient, and the application of an alternating magnetic field to inductively heat the magnetic material composition. The thermotherapeutic magnetic composition may also be administered by administering the ligand and the magnetic particle separately to the patient, and then combining the ligand and the magnetic particle in the patient's body.

In another embodiment, the treatment method comprises the administration of a thermotherapeutic magnetic composition, to a patient, detecting at least one location of accumulation of the magnetic composition within the patient's body, and the application of an alternating magnetic field to inductively heat the magnetic composition.

In another embodiment, the treatment method comprises the administration of a thermotherapeutic magnetic composition to a patient, and the application of an alternating magnetic field to induce a desired pathological effect by inductively heating the magnetic composition to cause a necrosis, an apoptosis, or a pathogen deactivation.

In another embodiment, the treatment method comprises the administration of a thermotherapeutic magnetic composition, which may be via intraperitoneal injection, intravascular injection, intramuscular injection, subcutaneous injection, topical, inhalation, ingestion, rectal insertion, wash, lavage or rinse perisurgically, or extracorporeal administration into patient's bodily materials.

Any of the disclosed embodiments for a treatment method may comprise the monitoring of at least one physical characteristic of a portion of a patient.

In any of the disclosed embodiments for a treatment method, the predetermined target may be associated with diseases, such as cancer, diseases of the immune system, pathogen-borne diseases, and undesirable targets, such as toxins, reactions to organ transplants, hormone-related diseases, and non-cancerous diseased cells or tissue.

The above summary of the present invention is not intended to describe each illustrated embodiment or every implementation of the present invention. The figures and the detailed description which follow particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
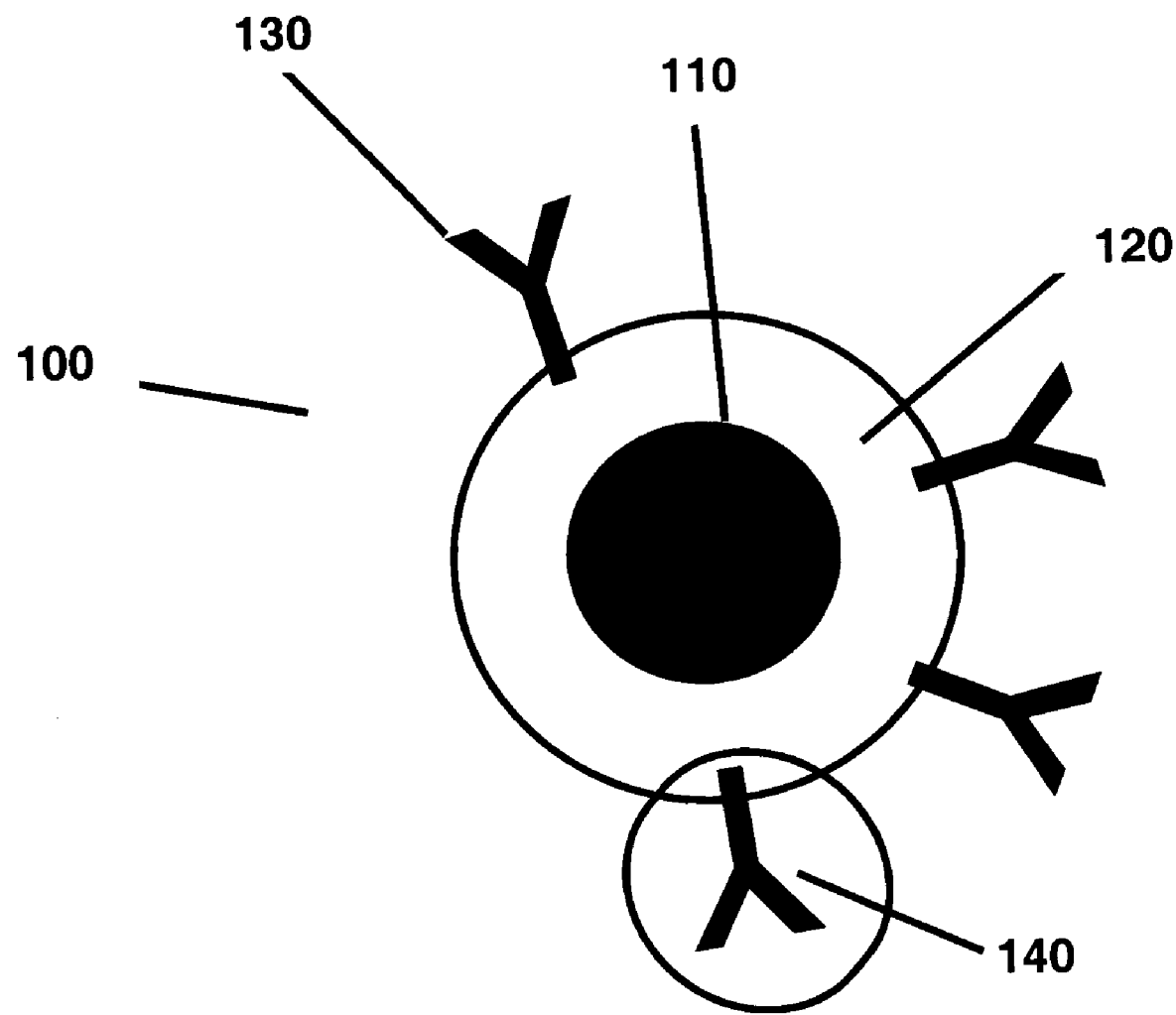
FIG. 1 schematically illustrates a bioprobe configuration, according to an embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF EXEMPLARY EMBODIMENTS

The present invention pertains to thermotherapeutic compositions for treating disease material, and methods for treating disease material utilizing such compositions. The compositions and methods of the present invention may be used for the treatment of a variety of indications, including cancer. The methods of therapy using the disclosed compositions comprise the administration to a patient a therapeutic magnetic composition that comprise bioprobes, and the application of an alternating magnetic field to an area of the patient containing the magnetic particle composition to heat the bioprobes sufficiently to kill targeted cells. The present invention, or aspects thereof, may be amenable to use in conjunction with suitable devices or apparatus.

DEFINITIONS

The term "AMF" (an abbreviation for alternating magnetic field), as used herein, refers to a magnetic field that changes the direction of its field vector periodically, typically in a sinusoidal, triangular, rectangular or similar shape pattern, with a frequency of in the range of from about 80 kHz to about 800 kHz. The AMF may also be added to a static magnetic field, such that only the AMF component of the resulting magnetic field vector changes direction. It will be appreciated that an alternating magnetic field is accompanied by an alternating electric field and is electromagnetic in nature.

The term "bioprobe", as used herein, refers to a targeted nanoparticle comprising a magnetic nanoparticle core, coating, linker, and targeting ligand, that is used to selectively treat tissue by heating in response to an alternating magnetic field (AMF). Additionally, the bioprobe may comprise a radioactive source or species that may become radioactive when exposed to an appropriate energy source. Yttrium-90 ($^{90}Y$) is an exemplary radioactive source. Boron-10 ($^{10}B$) is an exemplary species that may become radioactive when exposed to a suitable energy source and thereby becomes radioactive. Boron-10 ($^{10}B$) is becomes radioactive when exposed to a beam of neutrons because it possesses a high neutron absorption cross-section, and becomes radioactive upon capture of a neutron. The bioprobe may also comprise a chemotherapeutic agent. Doxorubicin is an exemplary chemotherapeutic agent.

The term "bioprobe system", as used herein, refers to a bioprobe specific to a target that is optionally identified via a marker.

The term "coating", as used herein, refers to a material, combination of materials, or covering of the magnetic nanoparticle, comprising a suitable biocompatible material that serves to affect in vivo transport of the bioprobe throughout the patient, and facilitates uptake and retention by diseased tissues and cell. A combination of dextran and polyethylene glycol is an exemplary coating.

The term "disease material", as used herein, refers to tissue or cells associated with cancer of any type, such as bone marrow, lung, vascular, neuro, colon, ovarian, breast and prostate cancer; diseases of the immune system, such as AIDS; pathogen-borne diseases, which can be bacterial, viral, parasitic, or fungal, examples of pathogen-borne diseases include HIV, tuberculosis and malaria; hormone-related diseases, such as obesity; vascular system diseases; central nervous system diseases, such as multiple sclerosis; and undesirable matter, such as adverse angiogenesis, restenosis, amyloidosis, toxins, reaction-by-products associated with organ transplants, and other abnormal cell or tissue growth.

The term "duty cycle", as used herein, refers to the ratio of the time that the energy source is on to the total time that the energy source is on and off in one on-off cycle.

The term "energy source", as used herein, refers to a device that is capable of delivering energy, of a form other than AMF, to the bioprobe for the purpose of activating a potential radioactive source comprising the bioprobe.

The term "indication", as used herein, refers to a medical condition, such as a disease. Breast cancer is an exemplary indication.

The term "ligand", as used herein, refers to a molecule or compound that attaches to a bioprobe and targets and attaches to a biological marker. A monoclonal antibody specific for HER-2 (an epidermal growth factor receptor protein) is an exemplary ligand.

The terms "linker" or "linker molecule," as used herein, refer to an agent that targets particular functional groups on a ligand and on a magnetic particle or a coating, and thus forms a covalent link between any two of these.

The term "magnetic nanoparticle", as used herein, refers to aggregates of magnetically coupled superparamagnetic grains, with characteristic relaxation time of the collective magnetic state appropriately tuned to inductively heat via magnetic hysteresis losses, e.g., Neél relaxation, in an alternating magnetic field.

The term "marker", as used herein, refers to an antigen or other substance to which the bioprobe ligand is specific. HER-2 protein is an exemplary marker.

The term "target", as used herein, refers to the matter for which deactivation, rupture, disruption or destruction is desired, such as a diseased cell, a pathogen, or other undesirable matter. A marker may be attached to the target. Breast cancer cells are exemplary targets.

The Targeted Therapy System

The targeted therapy system of the present invention involves the utilization of a bioprobe system in conjunction with at least one energy source to treat an indication.

The Bioprobe System.

Figure 2:
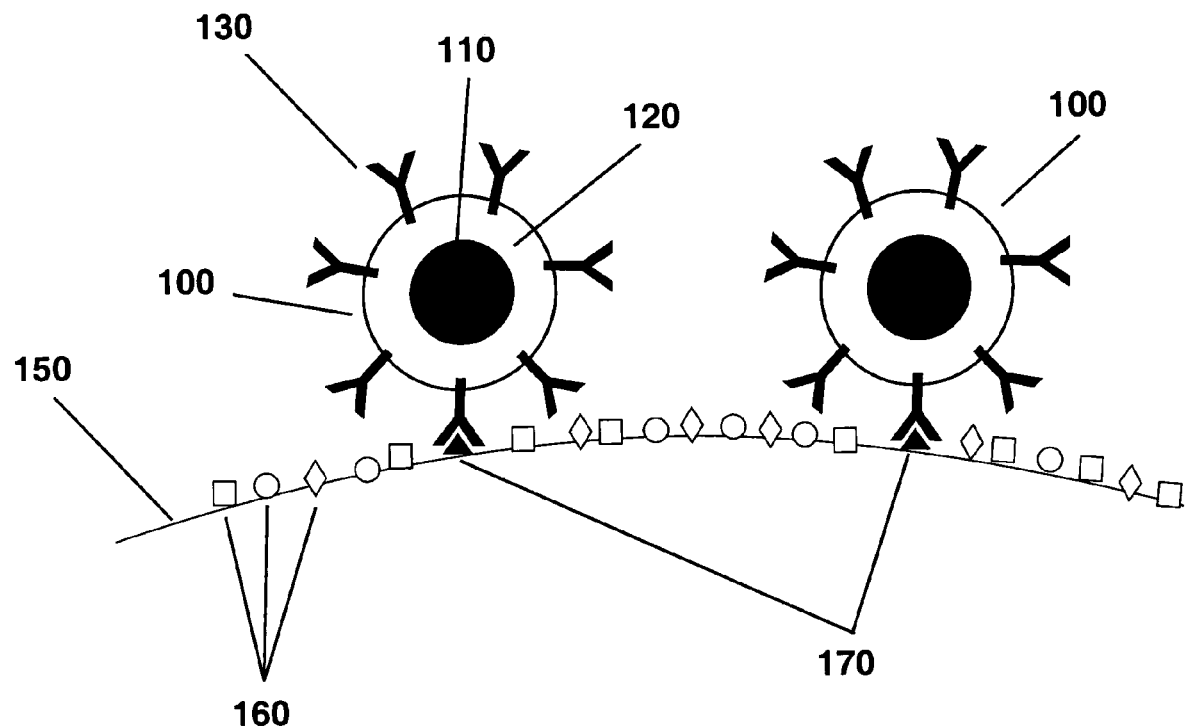
FIG. 2 schematically illustrates target specific bioprobes bound to a disease cell surface, according to an embodiment of the present invention.

Various embodiments of the bioprobe system of the present invention are demonstrated via FIG. 1 and FIG. 2. FIG. 1 illustrates a bioprobe configuration according to an embodiment of the present invention, wherein a bioprobe 100 comprises a magnetic nanoparticle 110. The magnetic nanoparticle 110 may comprise a coating 120. Heat may be generated in the magnetic nanoparticle 110 when the magnetic nanoparticle 110 is exposed to an AMF source through hysteresis. In addition, the magnetic nanoparticle may comprise a radioactive element, or a suitable isotope of an element that will become radioactive when exposed to a suitable, non-AMF, energy source.

Magnetic Nanoparticle

General Properties of Fine Magnetic Grains: Single Domains—Stable and Unstable

Nanoscale (having dimensions less than 1 μm) magnetic materials possess many enhanced properties, such as remanence and coercivity, as compared with their conventional or bulk counterparts. With decreasing grain size, an increasing fraction of atoms comprising the grain lieon the surface and interface regions. This increases the significance of the effect of the surface and interface electronic structure on the magnetic properties. The intrinsic magnetic properties of a material, such as spontaneous magnetization and magnetocrystalline anisotropy, are strongly influenced by the grain (crystal) size. Magnetocrystalline anisotropy is only one contribution to the total anisotropy energy of a single domain grain. Additional contributions may arise from magnetostatic, shape, stress, and surface anisotropies. The last of these is closely related to the detailed chemical nature of surface and grain boundary that become increasingly important as the size is reduced.

The total anisotropy energy may increase with decreasing grain size, within a certain size range, because of the growing surface anisotropy contribution. It is many of these enhanced magnetic properties that make nanoscale magnetic materials particularly well suited for a variety of applications. For the invention described herein, the enhanced magnetocrystalline anisotropy contributes to increased hysteretic losses of these materials when they are subjected to alternating magnetic fields (AMF), which in turn, results in much higher specific absorption rates (SAR), or heating. Indeed, nanoscale magnetic materials, within a certain size, can produce significantly higher SAR values for a given mass of material under particular AMF conditions because the total anisotropy energy may increase with decreasing grain size, due to the growing surface anisotropy contribution when compared with their bulk counterparts.

Single Non-Interacting Grains

It is understood that a large magnetic body is divided into uniformly magnetized regions, referred to as domains, that are separated by domain walls (Bloch walls) in order to minimize its magnetostatic energy. However, the energy that must be minimized is the total energy, including magnetostatic, exchange, and anisotropic components, as well as the domain wall contribution. Therefore, it is the final balance of energies that determines both the number and shape of magnetic domains within a magnetic material. As the size of a material is reduced, the size of domains will also be reduced. In addition, the structure of the domains may be changed as will the domain wall width and structure. There is an energy cost associated with domain wall formation; hence the resulting total energy balance will limit the subdivision of domains to a certain optimum number and size.

There is a corresponding lower limit in the grain size, below which a single-domain structure exists, because the energy increase due to the formation of domain walls is higher than the energy decrease obtained by dividing the single domain into smaller domains. For many magnetic materials, the dimensional limit is in the range of from about 2 nm to about 800 nm, depending on the spontaneous magnetization and on the anisotropy and exchange energies.

For a magnetic body that possesses only a single magnetic domain, i.e., a single magnetic domain grain, the behavior of the magnetic moment, m, a vector defining magnitude and direction of magnetization, of the magnetic domain with respect to time and its environment (temperature, external magnetic field, etc.) is governed by the total anisotropy energy of the magnetic grain. The orientation of the magnetic moment with respect to the crystalline axes is an explicit product of the anisotropy energy and physical environment, both past and present, in which the grain is placed. Among the environmental variables of general interest to the invention disclosed herein, are the presence and nature of a time varying magnetic field (AMF) and temperature. Specifically, it is the manner of response exhibited by the spatial orientation (reversal) of m in a single magnetic domain grain when placed in the presence of an AMF that determines hysteresis losses and consequently heat generated (SAR).

The potential of a single magnetic domain grain (crystal) to generate heat via hysteresis losses when exposed to an alternating magnetic field is determined by the balance of energies within the grain that leads to a total anisotropy energy. This sum of anisotropy energies presents an energy barrier, $E_B$, to changes in orientation of the magnetic moment, m, a vector representing both direction and magnitude of the net magnetism of the grain. Thus, the stability of m with respect to time increases with increasing values of $E_B$. The grain volume, V, and $E_B$ combine to define a characteristic relaxation time, $\tau_0$, which is the time required for spontaneous fluctuations, or relaxations, in the direction of m to some beginning value after it has been forcibly reoriented by a sufficiently strong magnetic field. Stated in another way, $\tau_0$ may be considered an intrinsic property of the grain and depends upon various parameters such as composition, volume, shape, etc. of the grain, and upon symmetries within the grain and upon the relaxation pathways available to m.

The amount of heat realized through hysteresis losses of a single domain grain when exposed to an alternating magnetic field is the result of a combination of both the intrinsic properties of the grain and experimental conditions. Experimental temperature will determine the relative difference between $E_B$ and energy available to the system, thus setting an experimental relaxation time, or $\tau$. This relationship may be defined mathematically as:

$$\tau = \tau_0 \exp\left(\frac{E_B}{kT}\right). \quad (1)$$

Thus, the relationship of the period of oscillation of the AMF, $1/\nu$, with $\tau$ becomes a critical experimentally observable quantity that leads directly to the amount of heat generated through hysteresis losses. Here, $\nu$ is the frequency of oscillation of the AMF. For $1/\nu \gg \tau$, the moment appears unblocked and spontaneously overcomes $E_B$ and reorients randomly without exhibiting hysteresis losses, i.e., no heat will be generated. Conversely, if $1/\nu \ll \tau$, the moment appears blocked and resists changes in orientation. With a sufficient magnitude of the AMF, m is forced to overcome $E_B$ and heat is released during the change.

Anisotropy energy, or potential hysteretic loss, in a single domain grain is proportional, in first approximation, to the volume of the grain. Thus, for large single magnetic domain grains the anisotropy energy may be so high that the energy barrier for magnetization reversal cannot be overcome by thermal energies for any temperature below the material's Curie temperature. Thermal energy is defined by the product kT where k is the Boltzmann constant and T is temperature in Kelvin. Such a single domain magnetic grain is said to have a stable single domain because magnetic moment does not fluctuate, and it can be said to exhibit intrinsically stable magnetic domain behavior with respect to time. Magnetization reversal may occur in such an intrinsically stable magnetic single domain if the grain is exposed to an external magnetic field that is sufficiently strong to overcome the anisotropy energy, and force a change or reversal of the magnetization vector (magnetic moment). Because the anisotropy energy represents a barrier to rotation of the magnetic moment, such a spatial change in this vector is accompanied by a release of energy in the form of heat. The amount of heat released is proportional, in a first approximation, to the anisotropy energy.

If the magnetic field is removed, the magnetic moment will retain the orientation imprinted by the magnetic field for a characteristic time. The time required for such an orientation change of the magnetic moment to occur after the field is removed is a relaxation time that is characteristic of the grain and is a consequence of both the anisotropy energy of the grain and kT. In the extreme case of intrinsically stable magnetic single domain grains, this time is greater than $10^9$ seconds. Hence, the magnetic moment appears blocked because the anisotropy energy presents an insurmountable barrier to spontaneous rotations of the magnetic spin system, for all temperatures up to the material Curie temperature. The Curie (or Néel) temperature is defined as the temperature at which a transition from ferromagnetic to paramagnetic state occurs.

Conversely, as the volume of a grain decreases within the single domain regime, so does the anisotropy energy. Below a certain characteristic grain size, the anisotropy energy may become so low as to be comparable to or lower than kT for any value of T above zero. This implies that the energy barrier for magnetization reversal may be overcome, and then the total magnetic moment of the grain can thermally fluctuate, similar to a single spin in a paramagnetic material. In this case, the entire spin system may spontaneously rotate, the spins within the single-domain particles remaining magnetically coupled. The orientation of the magnetization vector with respect to the crystalline axes fluctuates and is intrinsically unstable. This is superparamagnetism because of the similarity to paramagnetism observed in bulk materials. Such a magnetic single domain grain may be said to possess an intrinsically unstable single domain, or be intrinsically superparamagnetic.

Exposing a superparamagnetic grain to an external magnetic field will cause the magnetic moment to align in the direction of the magnetic field vector, but with no concomitant release of energy. Because the anisotropy energy is lower than kT for any experimental temperature measurably above zero, it does not present a barrier to magnetization reversal. When the magnetic field is removed from the grain, the spontaneous fluctuations of the orientation of the magnetic moment will rapidly destroy any imprint imposed by the external magnetic field. The characteristic relaxation time of an intrinsically superparamagnetic grain is very short, typically of order $10^{-9}$ seconds. In contrast to the intrinsically stable single domain grain, the magnetic moment of an intrinsically superparamagnetic material is unblocked at all experimental temperatures, and for all time dependent measurements for which the time is longer than the characteristic relaxation time.

Between these two extremes lies a range of grain volumes for which the anisotropy energy is intermediate, and thus the time scale of magnetization reversal depends explicitly upon the temperature and time scale of measurements. Thus, for a given grain volume, the relaxation time is defined by temperature, and hence the magnetic moment may appear blocked if the measurement time is shorter than the characteristic relaxation time. In this case, the material will exhibit behavior similar to a stable single domain and will generate heat if placed in an AMF with a period that is shorter than the characteristic relaxation time. Such a material may be defined as blocked and apparently stable single domain under these conditions.

Conversely, if the measurement time, i.e., AMF period, exceeds the characteristic relaxation time of the grain unblocked, or apparently superparamagnetic behavior will be observed. Because the characteristic relaxation time in this instance is much shorter than the time of measurement, or AMF period, magnetization reorientation and even reversal occurs randomly with no apparent impedance due to anisotropy energy barriers, and hence no concomitant release of heat.

Temperature is also critically important to distinguishing apparently stable single domain, or blocked, behavior from apparently superparamagnetic, or unblocked, behavior. Thus, by analogy, the characteristic relaxation time of the magnetic moment of a grain with specified volume possessing a single magnetic domain will appear blocked when exposed to an AMF of fixed period if the experimental temperature, $T_{exp}$, is below a characteristic value. If $T_{exp}$ is increased to a value above this characteristic temperature, the magnetic moment appears unblocked when exposed to an AMF of the same fixed period. This characteristic temperature may be defined as the blocking temperature, $T_b$. Thus, when a grain possessing a single magnetic domain is placed within an AMF of fixed frequency, the forced oscillations of the magnetic moment will release heat while the grain temperature is below the blocking temperature. Once the grain temperature exceeds the blocking temperature, the magnetic moment becomes unblocked, and any release of heat with further exposure to the AMF will cease. This is because the thermal energy, defined by kT, exceeds the anisotropy energy, thereby providing an excess of energy to the spin system to surmount the magnetocrystalline energy barrier.

Systems of Non-Interacting Grains

The above describes the behavior of an individual single magnetic domain grain of specified composition and volume. A bioprobe may comprise a magnetic nanoparticle that is itself an aggregate of more than one single domain magnetic grain. Further, the bioprobes may comprise a suspension of more than one bioprobe suspended in a suitable, and preferably non-magnetic, medium. Thus, the bioprobe suspension may be comprised of individual bioprobes of varying size, centered on a mean with a distribution. In turn, each bioprobe may comprise a magnetic nanoparticle comprised of more than one single magnetic domain grain that vary in volume, also centered about a mean with a distribution.

A full theoretical description of relaxation time and consequent hysteresis losses and generated heat in an applied AMF for a bioprobe suspension will necessitate inclusion of many more factors than those necessary to describe the behavior of individual single magnetic domain grains with specified volume, i.e., ensemble of monodisperse grains with non-interacting moments. Because volume is an intrinsic property of a single magnetic domain grain that directly affects $E_B$ a determination of $\tau_0$ and $\tau$, for an ensemble of grains comprising grains with varying volume requires knowledge of the size distribution. While the mean volume may be associated with a value of $E_B$ sufficient to block m at a specified temperature and AMF frequency, there may be a sizable fraction of grains in the ensemble with volume and $E_B$ significantly lower. The net effect may result in a measured heat output that may be significantly lower than that expected from knowledge of the mean volume alone. The converse also may be demonstrated. An ensemble of grains may possess a mean volume for which the value of $E_B$ is lower than that required to block m, i.e., it appears superparamagnetic. Consequently, the system would not be expected to exhibit hysteresis in an AMF with specified frequency at a specified temperature. However, this ensemble may contain a sizable number of grains with volume significantly greater than the mean. This component of the ensemble may appear blocked, resulting in hysteresis and a measurable quantity of heat that is generated when exposed to the experimental AMF with specific frequency at a specified temperature. The particular amount of heat generated may be substantial and apparently contradicting what might be predicted from knowledge of only the mean grain volume.

Interparticle interactions is another factor that is necessary to fully describe the hysteresis behavior of an ensemble of bioprobes comprising an ensemble of single magnetic domain grains. Magnetic forces are, by definition, long-range forces. That is, the range of influence may extend far beyond the boundary of a magnetic grain. Thus, a magnetic nanoparticle comprised of more than one single domain magnetic grain may exhibit properties greater than the sum of the magnetic properties of each grain, because of the additional contribution to the anisotropy energy that result from the collective state, i.e., interaction contributions of each domain m with others.

It has been experimentally established that interaction effects modify anisotropy energies to produce a collective state that may exhibit behavior uncharacteristic of the state of the individual grains, if non-interacting. It has often been observed that the result is an apparently increased $E_B$, resulting in an inhomogeneous blocking process. Thus, a magnetic nanoparticle comprised of a cluster of superparamagnetic grains may appear blocked, and even exhibit hysteresis, under appropriate experimental conditions. Because the blocking process is inhomogeneous, the hysteresis behavior may be considerably weaker than a single domain grain of volume comparable to the aggregate. Such an aggregate cannot be defined as either superparamagnetic or stable single domain, because it is neither in a strict sense under all conditions. Further, each of the grains comprising the aggregate is superparamagnetic in all respects and cannot exhibit hysteresis.

Precise definition and full characterization of a magnetic nanoparticle comprised of an aggregate of single magnetic domain grains, i.e., a combination of stable and superparamagnetic, or purely superparamagnetic, may be difficult and impractical because many measurement techniques are necessary for characterization. Indeed, results of some of these measurements may be inconclusive or even contradictory. Nevertheless, a practical measure does exist to define apparent behavior for the purpose of the invention described herein. An ensemble of bioprobes, wherein each bioprobe may be comprised of an ensemble of magnetic nanoparticles, and each magnetic nanoparticle, further comprised of either individual grains or an aggregate of grains, can be defined by the aggregate mean anisotropy energy, which then defines the mean characteristic relaxation time and mean behavior in a specific AMF given a specific temperature. Therefore, it is possible to define the magnetic properties of such an ensemble of bioprobes in a relatively simple manner. Based on experimental temperatures between 270 K and 380 K, and exposure to an AMF with a frequency in the range of from about 100 kHz to about 600 kHz and an amplitude in the range of from about 7.98 kA/m to about 104 kA/m, measurement of the SAR is used to distinguish the apparently blocked from the apparently unblocked behavior of the entire ensemble. An ensemble of unblocked, or apparently superparamagnetic, particles will generate less than 10 W/g particle under the specified conditions. By comparison, an ensemble of non-interacting intrinsically superparamagnetic nanoparticles will generate exactly 0 W/g particles, by definition. Conversely, apparently blocked bioprobes will generate between 10 W/g to 150 W/g particle. Further, an ensemble of intrinsically blocked, or stable single domain, particles will generate greater than 150 W/g particle under the specified conditions via hysteresis heating, even though some superparamagnetic contamination may exist.

Radioactive Isotopes

Because of the synergistic effects of radiation and heat for treating a disease, particularly cancer, the effectiveness of targeted thermotherapy may be significantly enhanced if the bioprobes comprise, a radioactive isotope. In this manner, the radiation may be delivered at typical doses, from about 20 Gy to about 60 Gy, or preferably at sub-lethal doses (less than 20 Gy) and become lethal only after the thermotherapy has been initiated or completed. The dose level of radiation may be controlled by controlled incorporation of the radioactive isotope in the bioprobe composition. Further controls of the radiation dose may be achieved via the use of a bioprobe suspension that comprises a mixture of radioactively-labeled bioprobes with "unlabeled" bioprobes. Any radioactive isotope currently in use for the treatment of disease, or those developed in the future, may be suitable for use herein to enhance the therapeutic ratio of the targeted thermotherapy. Examples of suitable radioactive isotopes are, but not limited to, iodine-131, cobalt-60, iridium-192, yttrium-90, strontium-89, samarium-153, rhenium-186, and technetium-99m.

Potentially Radioactive Isotopes

Certain isotopes comprise unstable nuclei (non-radioactive) that possess a high absorption cross-sections for certain subatomic particles, i.e., neutrons, protons, etc., and for certain forms of ionizing radiation, i.e., x-rays. When the nuclei of these isotopes absorb the radiation or particle, the nucleus becomes unstable and thus emits radiation as it decays. This phenomenon has already been recognized and used for the treatment of cancer. The most notable example is boron (boron-10) neutron capture therapy for the treatment of cancer.

Such treatments have not gained wider acceptance because the level of radiation emitted by the isotope may be insufficient to produce a lethal dose to a tumor. However, as a component of a bioprobe, the delivery of the isotope is both targeted and its radiation initiated only in a sequence with thermotherapy that will maximize the synergy of the two energy forms. Consequently, the radiation becomes more cytotoxic when used in combination with thermotherapy.

Other isotopes possessing high neutron absorption cross sections include many of the lanthanides, such as samarium-149, gadolinium-157, and gadolinium-155. Samarium is particularly advantageous in that it is magnetic, and its incorporation into the magnetic nanoparticle crystalline structure may enhance the magnetic properties of the nanoparticle.

Chemotherapeutic Agents

As with radioactive isotopes, bioprobes comprising chemotherapeutic agents may synergistically combine with the targeted thermotherapy to enhance a therapeutic outcome. Examples of chemotherapeutic agents suitable for use herein include, but not limited to, doxorubicin, platinum complexes, such as cisplatin, etc.

Imaging Isotopes

There are various techniques of imaging isotopes that are suitable for use herein, particularly MRI, PET, SPECT, and Bioimpedance.

Small paramagnetic or superparamagnetic particles of ferrite (iron oxide $Fe_3O_4$ or $Fe_2O_3$) can be used as paramagnetic contrast medium in magnetic resonance imaging (MRI). These agents exhibit strong T1 relaxation properties, and due to susceptibility differences to their surroundings, they also produce a strongly varying local magnetic field that enhances T2 relaxation to darken the contrast media-containing structures. Very small particles of less than 300 nanometers also remain intravascular for a prolonged period of time. The agents are also referred to as SPIO's ("small particle iron oxides" or "superparamagnetic iron oxides") and USPIO's ("ultrasmall particle iron oxides" or "ultrasmall superparamagnetic iron oxides"). In one embodiment of the present invention, targeted thermotherapy and MRI are combined. MRI contrast isotopes that target vulnerable plaques, such as Gadolinium-labeled antifibrin nanoparticles, are used. Once these nanoparticles are uptaken by the plaque, AMF is used for destroying the plaque.

Positron emission tomography (PET) is a technique for measuring the concentrations of positron-emitting radioisotopes within the tissue of living patients. A wide range of compounds can be used with PET. These positron-emitting radionuclides have short half-lives and high radiation energies. The primary positron-emitting radionuclides used in PET include Carbon-11, Nitrogen-13, Oxygen-15, and Fluorine-18, with half-lives of 20 min, 10 min, 2 min, and 110 min, respectively. These compounds are commonly known in PET as tracer compounds.

Single photon emission computed tomography (SPECT) involves the detection of gamma rays emitted singly from radioactive atoms, called radionuclides, such as Technetium-99m and Thallium-201. A radiopharmaceutical is a protein or an organic molecule that has a radionuclide attached to it. The proteins and organic molecules are selected based on their use or absorption properties within the human body. SPECT is used routinely to help diagnose and stage cancer, stroke, liver disease, lung disease and a host of other physiological (functional) abnormalities.

Radioimmunological imaging radionuclides, such as Molybdenum-99, Technetium-99m, Chromium-51, Copper-64, Dysprosium-165, Ytterbium-169, Indium-111, Iodine-125, Iodine-131, Iridium-192, Iron-59, Phosphorus-32, Potassium-42, Rhodium 186, Rhenium-188, Samarium-153, Selenium-75, Sodium-24, Strontium-89, Xenon-133, Xenon-127, Yttrium-90 or others, are bound to antibodies (sometimes referred to as labeling, tracing or tagging) that will bind to a specific antigenic target. In one embodiment of the present invention, radioimmunological imaging is combined with targeted thermotherapy by attaching the radionuclides directly to the bioprobes. In such a configuration, the uptake process of the bioprobes can be directly imaged.

Bioimpedance is a measure of how well the body impedes electric current flow. Fat has high resistivity, blood lower resistivity. Impedance is measured by applying a small electric current, for example, using two electrodes, and measuring the resulting small voltage with another pair of electrodes. The lower the voltage is, the lower the tissue impedance will be for a given current. Tissue consists of cells and membranes; membranes are thin but have a high resistivity and electrically behave as small capacitors. At high frequencies, the result becomes independent of the capacities of the cell membranes. At low frequencies, however, the membranes impede current flow, and the results are dependent on liquids outside the cells.

In one embodiment of the present invention, one or more of these imaging techniques is used to image the uptake of the bioprobes prior to, during, or after targeted therapy administration.

Coating

Coating 120 may enhance the heating properties of bioprobe 100, particularly if coating 120 is a polymeric material. Coating 120 may also comprise radioactive or potentially radioactive elements.

Suitable materials for the coating 120 include synthetic and biological polymers, copolymers and polymer blends, and inorganic materials. Polymer materials may include various combinations of polymers of acrylates, siloxanes, styrenes, acetates, akylene glycols, alkylenes, alkylene oxides, parylenes, lactic acid, and glycolic acid. Further suitable coating materials include a hydrogel polymer, a histidine-containing polymer, and a combination of a hydrogel polymer and a histidine-containing polymer.

Coating materials may also include combinations of biological materials, such as a polysaccharide, a polyaminoacid, a protein, a lipid, a glycerol, and a fatty acid. Examples of other biological materials suitable for use herein include heparin, heparin sulfate, chondroitin sulfate, chitin, chitosan, cellulose, dextran, alginate, starch, carbohydrate, and glycosaminoglycan. Examples of proteins useful herein include an extracellular matrix protein, proteoglycan, glycoprotein, albumin, peptide, and gelatin. These materials may also be used in combination with any suitable synthetic polymer material.

Inorganic coating materials may include any combination of a metal, a metal alloy, and a ceramic. Examples of ceramic materials suitable for use herein include a hydroxyapatite, silicon carbide, carboxylate, sulfonate, phosphate, ferrite, phosphonate, and oxides of Group IV elements of the Periodic Table of Elements. These materials may form a composite coating that may also contain one or more biological or synthetic polymers. Where the magnetic particle 110 is formed from a magnetic material that is biocompatible, the surface of the particle itself operates as the biocompatible coating.

The coating material may also serve to facilitate transport of the bioprobe 100 into a cell, a process known as transfection. Such coating materials, referred to as transfection agents, include vectors, prions, polyaminoacids, cationic liposomes, amphiphiles, and non-liposomal lipids or any combination thereof. A suitable vector may be a plasmid, a virus, a phage, a viron, a viral coat. The bioprobe coating may be a composite of any combination of transfection agent with organic and inorganic materials, such that the particular combination may be tailored for a particular type of a diseased material and a specific location within a patient's body.

Markers

The choice of a marker (antigen) 160 and 170, as illustrated in FIG. 2, may be important in the targeted therapy methods of the present invention. Although not limited thereto, use and selection of markers is most prevalent in cancer immunotherapy. For breast cancer and its metastases, a specific marker or markers may be selected from cell surface markers such as, for example, members of the MUC-type mucin family, an epithelial growth factor (EGFR) receptor, a carcinoembryonic antigen (CEA), a human carcinoma antigen, a vascular endothelial growth factor (VEGF) antigen, a melanoma antigen (MAGE) gene, family antigen, a T/Tn antigen, a hormone receptor, growth factor receptors, a cluster designation/differentiation (CD) antigen, a tumor suppressor gene, a cell cycle regulator, an oncogene, an oncogene receptor, a proliferation marker, an adhesion molecule, a proteinase involved in degradation of extracellular matrix, a malignant transformation related factor, an apoptosis related factor, a human carcinoma antigen, glycoprotein antigens, DF3, 4F2, MGFM antigens, breast tumor antigen CA 15-3, calponin, cathepsin, CD 31 antigen, proliferating cell nuclear antigen 10 (PC 10), and pS2.

For other forms of cancer and their metastases, a specific marker or markers may be selected from cell surface markers such as, for example, a member of vascular endothelial growth factor receptor (VEGFR) family, a member of carcinoembryonic antigen (CEA) family, a type of anti-idiotypic mAB, a type of ganglioside mimic, a member of cluster designation/differentiation antigens, a member of epidermal growth factor receptor (EGFR) family, a type of a cellular adhesion molecule, a member of MUC-type mucin family, a type of cancer antigen (CA), a type of a matrix metalloproteinase, a type of glycoprotein antigen, a type of melanoma associated antigen (MAA), a proteolytic enzyme, a calmodulin, a member of tumor necrosis factor (TNF) receptor family, a type of angiogenesis marker, a melanoma antigen recognized by T cells (MART) antigen, a member of melanoma antigen encoding gene (MAGE) family, a prostate membrane specific antigen (PMSA), a small cell lung carcinoma antigen (SCLCA), a T/Tn antigen, a hormone receptor, a tumor suppressor gene antigen, a cell cycle regulator antigen, an oncogene antigen, an oncogene receptor antigen, a proliferation marker, a proteinase involved in degradation of extracellular matrix, a malignant transformation related factor, an apoptosis-related factor, a type of human carcinoma antigen.

In one embodiment of the invention, a bioprobe includes one or more ligands 130 targeting the MUC-1 receptor of the mucin family. In yet another embodiment, a bioprobe has one or more ligands 130 targeting at least one of the EGFR family, such as HER-1, HER-2, HER-3 and HER-4. MUC-1 (Human epithelial mucin, CD277), is a high molecular weight, transmembrane mucin glycoprotein expressed by most glandular and epithelial cell lineages. In addition, MUC-1 has a large extracellular domain, portions of which may be shed into the bloodstream. MUC-1 may have a protective role, as its extracellular domain forms elongated rigid structures extending above other molecules on the cell. MUC-1 also plays a role in cell-cell and cell-substrate adhesion. MUC-1 is highly expressed in many human adenocarcinomas, including 80% of breast cancers, and is associated with poor prognosis. Mucin (MUC-1 and MUC-2) expression is associated with tumor invasiveness. MUC-1 and MUC-2 expression is associated with invasive ductive carcinoma of the breast. MUC-1 is also present at high levels on many mylomas. Different tissues/cells produce differing glycoforms of MUC-1. Glycosylation of MUC-1 in malignant cells is often altered compared to normal tissue. MUC-1 is considered a truly tumor specific antigen, although it is also found on normal cells, its aberrant glycosylation on tumors creates new epitopes for targeting. The extracellular domain of MUC-1 may be shed into the blood stream. The ligand 130 may target the unshed remainder of the MUC-1 expressed on the cell surface.

Overexpression of growth factor receptors such as the EGFR family is indicated in tumors and has been associated with increased cell resistance to the cytotoxic effects of macrophages and cytotoxic factors, such as TNF (tumor necrosis factor), which can lead to tumor growth. The protein encoded by the HER-1/neu gene is a 170,000 Dalton protein, referred to as HER-1. The protein encoded by the HER-2/neu gene is a 185,000 Dalton protein referred to as HER-2. Both proteins have an intracellular domain, a transmembrane domain that includes two cysteine-rich repeat clusters, and an intracellular kinase domain. The extracellular domain of HER-2 may be shed into the bloodstream. Thus, ligand 130 may target the unshed remainder of the HER-2 expressed on the surface of the cell.

For ovarian cancers and their metastases, a specific marker or markers may be selected from cell surface markers such as, for example, one of ERBB2 (HER-2) antigen and CD64 antigen. For ovarian and/or gastric cancers and their metastases, a specific marker or markers may be selected from cell surface markers such as, for example, a polymorphic epithelial mucin (PEM). For ovarian cancers and their metastases, a specific marker or markers may be selected from cell surface markers such as, for example, one of cancer antigen 125 (CA125) or matrix metalloproteinase 2 (MMP-2). For gastric cancers and their metastases, a specific marker or markers may be selected from cell surface markers such as, for example, one of CA 19-9 antigen and CA242 antigen.

For non small-cell lung cancer (NSCLC), colorectal cancer (CRC) and their metastases, a specific marker or markers may be selected from cell surface markers such as, for example, vascular endothelial growth factor receptor (VEGFR), anti-idiotypic mAb, and carcinoembryonic antigen (CEA) mimic. For at least one of small-cell lung cancer (SCLC), malignant melanoma, and their metastases, a specific marker or markers may be selected from cell surface markers such as, for example, anti-idiotypic mAB or GD3 ganglioside mimic. For melanoma cancers and their metastases, a specific marker or markers may be selected from cell surface markers such as, for example, a melanoma associated antigen (MAA). For small cell lung cancers and their metastases, a specific marker or markers may be selected from cell surface markers such as, for example, a small cell lung carcinoma antigen (SCLCA).

For colorectal cancer (CRC) and/or locally advanced or metastatic head and/or neck cancer, a specific marker or markers may be selected from cell surface markers such as, for example, epidermal growth factor receptor (EGFR). For Duke's colorectal cancer (CRC) and its metastases, a specific marker or markers may be selected from cell surface markers such as, for example, Ep-CAM antigen.

For non-Hodgkin's lymphoma (NHL) and its metastases, a specific marker or markers may be selected from cell surface markers such as, for example, cluster designation/differentiation (CD) 20 antigen or CD22 antigen. For B-cell chronic lymphocytic leukaemia and associated metastases, a specific marker or markers may be selected from cell surface markers such as, for example, CD52 antigen. For acute myelogenous leukaemia and its metastases, a specific marker or markers may be selected from cell surface markers such as, for example, CD33 antigen.

For prostate cancers and their metastases, a specific marker or markers may be selected from cell surface markers such as, for example, prostate membrane specific antigen (PMSA). For carcinomatous meningitis and their metastases, a specific marker or markers may be selected from cell surface markers such as, for example, one of a vascular endothelial growth factor receptor (VEGFR) or an epithelial associated glycoprotein, for example, HMFGI (human milk fat globulin) antigen.

For lung, ovarian, colon, and melanoma cancers and their metastases, a specific marker or markers may be selected from cell surface markers such as, for example, B7-H1 protein. For colon, breast, lung, stomach, cervix, and uterine cancers and their metastases, a specific marker or markers may be selected from cell surface markers such as, for example, TRAIL Receptor-1 protein, a member of the tumor necrosis factor receptor family of proteins. For ovarian, pancreatic, non-small cell lung, breast, and head and neck cancers and their metastases, a specific marker or markers may be selected from cell surface markers such as, for example, EGFR (epidermal growth factor receptor).

For anti-angiogenesis targeting of tumor blood supply, a specific marker or markers may be selected from cell surface markers such as, for example, Integrin $\alpha v \beta 3$, a cell surface marker specific to endothelial cells of growing blood vessels.

For targeting of colon and bladder cancer and their metastases, a specific marker or markers may be selected from cell surface markers such as, for example, RAS, a signaling molecule that transmits signals from the external environment to the nucleus. A mutated form of RAS is found in many cancers.

In one embodiment of the present invention, ligand 130 targets a predetermined target associated with a disease of the patient's immune system. The particular target 150 and one or more ligands 130 may be specific to, but not limited to, the type of the immune disease. The ligand 130 may have an affinity for a cell marker or markers of interest. The marker or markers 160/170 may be selected such that they represent a viable target on T cells or B cells of the patient's immune system. The ligand 130 may have an affinity for a target associated with a disease of the patient's immune system such as, for example, a protein, a cytokine, a chemokine, an infectious organism, and the like.

For diseases of the patient's immune system, a specific marker or markers 160/170 may be selected from cell surface markers. The targeted cells may be T or B cells of the immune system. For rheumatoid arthritis, a specific marker or markers may be selected from cell surface markers such as, for example, one of CD52 antigen, tumor necrosis factor (TNF), and CD25 antigen. For rheumatoid arthritis and/or vasculitis, a specific marker or markers may be selected from cell surface markers such as, for example, CD4 antigen. For vasculitis, a specific marker or markers may be selected from cell surface markers such as, for example, CD18 antigen. For multiple sclerosis, a specific marker or markers may be selected from cell surface markers such as, for example, CD52 antigen.

In another embodiment, ligand 130 targets a predetermined target 150 associated with a pathogen-borne condition. The particular target 150 and ligand 130 may be specific to, but not limited to, the type of the pathogen-borne condition. A pathogen is defined as any disease-producing agent such as, for example, a bacterium, a virus, a microorganism, a fungus, and a parasite. The ligand 130 may have an affinity for the pathogen or pathogen associated matter. The ligand 130 may have an affinity for a cell marker or markers associated with a pathogen-borne condition. The marker or markers may be selected such that they represent a viable target on infected cells.

For a pathogen-borne condition, the ligand 130 for therapy utilizing bioprobes may be selected to target the pathogen itself. For a bacterial condition, a predetermined target may be the bacteria itself, for example, one of *Escherichia coli* or *Bacillus anthracis*. For a viral condition, a predetermined target may be the virus itself, for example, one of Cytomegalovirus (CMV), Epstein-Barr virus (EBV), a hepatitis virus, such as Hepatitis B virus, human immunodeficiency virus, such as HIV, HIV-1, or HIV-2, or a herpes virus, such as Herpes virus 6. For a parasitic condition, a predetermined target may be the parasite itself, for example, one of *Trypanasoma cruzi, Kinetoplastid, Schistosoma mansoni, Schistosoma japonicum* or *Schistosoma brucei*. For a fungal condition, a predetermined target may be the fungus itself, for example, one of *Aspergillus, Cryptococcus neoformans* or *Rhizomucor.*

For a pathogen-borne condition, the ligand 130 for therapy utilizing bioprobes may be selected to target cell markers of pathogen infected cells. For the HIV virus, the predetermined target may be CTLA4 expressed on the surface of HIV infected T cells. CTLA4 migrates to the infected cell's outer surface when the HIV virus is ready to be released.

In another embodiment, ligand 130 targets a predetermined target associated with an undesirable target material. The particular target 150 and ligand 130 may be specific to, but not limited to, the type of the undesirable target. An undesirable target is a target that may be an undesirable material. Undesirable material is material associated with a disease or an undesirable condition, but which may also be present in a normal condition. For example, the undesirable material may be present at elevated concentrations or otherwise be altered in the disease or undesirable state. The ligand 130 may have an affinity for the undesirable target or for biological molecular pathways related to the undesirable target. The ligand 130 may have an affinity for a cell marker or markers associated with the undesirable target material.

For an undesirable target, the selection of a predetermined target 150 may be important in the therapeutic methods of the present invention. Ligand 130 is selected to target biological matter associated with a disease or undesirable condition. For arteriosclerosis, a predetermined target may be, for example, apolipoprotein B on low density lipoprotein (LDL). An undesirable material may be adipose tissue or cellulite for obesity, associated with obesity, or a precursor to obesity. A predetermined marker or markers for obesity maybe selected from cell surface markers such as, for example, one of gastric inhibitory polypeptide receptor and CD36 antigen. Another undesirable predetermined target may be clotted blood.

In another embodiment, ligand 130 targets a predetermined target associated with a reaction to an organ transplanted into the patient. The particular target 150 and ligand 130 may be specific to, but not limited to, the type of organ transplant. The ligand 100 may have an affinity for a biological molecule associated with a reaction to an organ transplant. The ligand 130 may have an affinity for a cell marker or markers associated with a reaction to an organ transplant. The marker or markers may be selected such that they represent a viable target on T cells or B cells of the patient's immune system.

For reaction to a transplanted organ, ligand 130 is selected to target the immune response to a transplant. The transplanted organ may be treated before or after transplantation. For kidney transplantation, a predetermined marker or markers may be selected from cell surface markers such as, for example, human T cell receptor (CD3) antigen or CD18 antigen. For kidney and bone marrow transplantation, a predetermined marker or markers may be selected from cell surface markers such as, for example, CD52 antigen. For liver and bone marrow transplantation, a predetermined marker or markers may be selected from cell surface markers such as, for example, one of CD154 antigen and CD8 antigen. For transplantation tolerance, a predetermined marker or markers may be selected from cell surface markers such as, for example, CD4. For bone marrow, a predetermined marker or markers may be selected from cell surface markers such as, for example, CD52 antigen for efficient depletion of T cells from bone marrow before transplantation in order to avoid graft versus host disease. For xenotransplantation or xenografting, a predetermined marker or markers may be, for example, galactose. Galactose is known to be on pig organs, but is not present in humans.

In another embodiment, ligand 130 targets a predetermined target associated with a toxin in the patient. A toxin is defined as any poison produced by an organism including, but not limited to, bacterial toxins, plant toxins, insect toxin, animal toxins, and man-made toxins. The particular target 150 and ligand 130 may be specific to, but not limited to, the type of toxin. The ligand 130 may have an affinity for the toxin or a biological molecule associated with a reaction to the toxin. The ligand 130 may have an affinity for a cell marker or markers associated with a reaction to the toxin.

For a toxin in the patient, ligand 130 is selected to target the toxin. A bacterial toxin target may be, for example, one of Cholera toxin, Diphtheria toxin, and *Clostridium* botulinus toxin. An insect toxin may be, for example, bee venom. An animal toxin may be, for example, snake toxin, for example, *Crotalus durissus terrificus* venom.

In another embodiment, ligand 130 targets a predetermined target associated with a hormone-related disease. The particular target 150 and ligand 130 may be specific to, but not limited to, a particular hormone disease. The ligand 130 may have an affinity for a hormone or a biological molecule associated with the hormone pathway. The ligand 130 may have an affinity for a cell marker or markers associated with the hormone disease.

For a hormone related diseases, ligand 130 is selected to target a cell marker or markers. For estrogen-related disease or conditions, a predetermined target may be, for example, estrogen or cell surface marker or markers such as, for example, estrogen receptor. For human growth hormone disease, the predetermined target may be, for example, human growth hormone.

In another embodiment, ligand 130 targets a predetermined target associated with non-cancerous disease material. The particular target 150 and ligand 130 may be specific to, but not limited to, a particular non-cancerous disease material. The ligand 130 may have an affinity for a biological molecule associated with the non-cancerous disease material. The ligand 130 may have an affinity for a cell marker or markers associated with the non-cancerous disease material.

For non-cancerous disease material, the ligand 130 is selected to target a predetermined target such as, for example, one of non-cancerous diseased deposits and precursor deposits. For Alzheimer's disease, a predetermined target may be, for example, amyloid B protein and its deposits, or apolipoprotein and its deposits.

In another embodiment, ligand 130 targets a proteinaceous pathogen. The particular target 150 and ligand 130 may be specific to, but not limited to, a particular proteinaceous pathogen. The ligand 130 may have an affinity for a proteinaceous pathogen or a biological molecule associated with the proteinaceous pathogen. The ligand 130 may have an affinity for a cell marker or markers associated with the proteinaceous pathogen. For prion diseases also known as transmissible spongiform encephalopathies, a predetermined target may be, for example, Prion protein 3F4.

Ligands

In one embodiment of the present invention, at least one targeting ligand 130, such as, but not limited to, an antibody, is located on an exterior portion of bioprobe 100, as illustrated in FIG. 1. Targeting ligand 130 is selected to seek out and attach to a target 150.

FIG. 2 illustrates an embodiment wherein a bioprobe 100, comprising a susceptor 110, that comprises a coating 120, is attached to a target (such as a cell) 150 by one or more targeting ligands 130. Ligands 130 may also comprise radioactive or potentially radioactive elements.

Cell comprising target 150 may express several types of markers 160 and 170. The specificity of bioprobe 100 is represented by its attachment to targeted marker 160 over the many other markers or molecules 160 on cell comprising target 150. One or more bioprobes 100 may attach to the cell via ligand 130. Ligand 130 may be adapted, and bioprobe 100 may be designed such that bioprobe 100 remains externally on cell 150 or may be internalized into cell comprising target 150. Once bound to cell 150, the magnetic nanoparticle 110 heats in response to the energy absorbed. For example, the magnetic nanoparticle 110 may heat through hysteresis losses in response to an AMF. The heat may pass through coating 120 or through interstitial regions to the cell 150, for example via convection, conduction, radiation, or any combination of these heat transfer mechanisms. The heated cell 150 becomes damaged, preferably in a manner that causes irreparable damage. When bioprobe 100 becomes internalized within cell comprising target 150, bioprobe 100 may heat cell 150 internally via convection, conduction, radiation, or any combination of these heat transfer mechanisms. When a sufficient amount of energy is transferred by bioprobe 100 to cell 150, cell 150 dies via necrosis, apoptosis or another mechanism.

Suitable ligands for use herein include, but are not limited to, proteins, peptides, antibodies, antibody fragments, saccharides, carbohydrates, glycans, cytokines, chemokines, nucleotides, lectins, lipids, receptors, steroids, neurotransmitters, Cluster Designation/Differentiation (CD) markers, and imprinted polymers and the like. The preferred protein ligands include, for example, cell surface proteins, membrane proteins, proteoglycans, glycoproteins, peptides and the like. The preferred nucleotide ligands include, for example, complete nucleotides, complimentary nucleotides, and nucleotide fragments. The preferred lipid ligands include, for example, phospholipids, glycolipids, and the like.

In one embodiment of the present invention, the ligand 130 may be covalently bonded to or physically interacted with the magnetic particle 110 or the coating 120. The ligand 130 may be bound covalently or by physical interaction directly to an uncoated portion of the magnetic particle 110. The ligand 130 may be bound covalently or by physical interaction directly to an uncoated portion of the magnetic particle 110 and partially covered by the coating 120. The ligand 130 may be bound covalently or by physical interaction to a coated portion of the bioprobe 100. The ligand 130 may be intercalated to the coated portion of bioprobe 100.

Covalent bonding may be achieved with a linker molecule. Examples of functional groups used in linking reactions include amines, sulfhydryls, carbohydrates, carboxyls, hydroxyls and the like. The linking agent may be a homobifunctional or heterobifunctional crosslinking reagent, for example, carbodiimides, sulfo-NHS esters linkers and the like. The linking agent may also be an aldehyde crosslinking reagent such as glutaraldehyde. The linking agent may be selected to link ligand 100 to the magnetic particle 110 or the coating 120 in a preferable orientation, specifically with the active region of the ligand 150 available for targeting. Physical interaction does not require the linking molecule and the ligand 100 be bound directly to the magnetic particle 110 or to the coating 120 by non-covalent means such as, for example, absorption, adsorption, or intercalation.

Some exemplary embodiments of the bioprobe system, along with associated indications for which they may be utilized, are presented in Table 1.

TABLE 1

Bioprobe Systems and Indications

| TARGET | MARKER | LIGAND | INDICATION |
|---|---|---|---|
| Endothelial cells of growing blood vessels of metastatic cancer cells | Integrin vβ3 | Ber EP4 antibody LM609 antibody Integrin antagonist | Metastatic breast cancer, metastatic colon carcinoma |
| Cancer cells | Unglycosylated DF3 antigen | Anti-DF3 antibody | Breast cancer |
| Cancer cells | Kallikreins | Anti-kallikrein antibody | Ovarian and prostate cancer |
| Cancer cells | ErbB2 (HER-2/neu) | Anti-ErbB2 antibody, and scFv (F5), IDM-1 (aka MDX-210) variants | Breast and ovarian cancers |
| Cancer cells | Prostate specific membrane antigen (PSMA) | MDX-070 and 7E11-C5.3 antibodies | Prostate cancer |
| MCF-7 breast cancer cells | 43 Kd membrane associated glycoprotein | 323/A3 antibody | Breast cancer |
| Receptor tyrosine kinases-- FLT1 FLK1 | Vascular endothelial growth factor (VEGF) and VEGFB and placental growth factor receptors (PGFR) | Anti-FLT1 antibody Anti-FLK1 antibody, 2C3 antibody | Tumour angiogenesis Tumour angiogenesis |
| Metastatic cancer cells | CAR (coxsackie adenovirus cell-surface receptor) | Anti-CAR antibody | Metastatic prostate cancer |
| Vascular smooth muscle cells of cancer cells | Urokinase type plasminogen activator receptor (uPAR) | Urokinase type plasminogen activator (uPA) | Cancer |
| Blood vessels of cancer cells | Plasminogen activator inhibitor 1(PAI-1) | Anti-PAI-1 antibody | Breast cancer |
| Epithelial ovarian tumour cells | Matrix metaloproteinase 9 (MMP-9) | Anti-MMP-9 antibody | Ovarian carcinomas with lymph node metastasis. |
| Cancer cells | Cyclin A | Anti-cyclin A antibody | Squamous cell carcinoma of the tongue |
| Cancer cells | Cyclin D | Anti-cyclin D(1,2,3) antibody | Malignant breast cancer, head and neck squamous cell carcinomas, mantle cell carcinomas, laryngeal squamous cell carcinomas |
| Kidney cortex tissue | Cyclin E | Anti-cyclin E antibody | Human renal cell carcinoma |
| Tumorigenic human breast epithelial cells | Cyclin E | Anti-cyclin E antibody | Breast cancer |
| Malignant epithelial bladder tissue | Cyclin E | Anti-cyclin E antibody | Transitional cell carcinoma of the urinary bladder |
| Cancer cells | Cdc 2 | Anti-cdc 2 antibody | Breast cancer |
| Malignant epithelial bladder tissue | P27 | Anti-phospho p27 antibody | Transitional cell carcinoma of the urinary bladder |

TABLE 1-continued

Bioprobe Systems and Indications

BIOPROBE SYSTEM

| TARGET | MARKER | LIGAND | INDICATION |
|---|---|---|---|
| Cancer cells | P73 | Anti-p73 antibody | Lung carcinogenesis, bladder carcinogenesis, neuroblastoma, breast cancer |
| Cancer cells | Ras | Anti-ras antibody | Breast cancer |
| Cancer cells | c-myc | Anti C-myc antibody | Breast cancer |
| Cancer cells | c-fms | Anti-c-fms antibody | Breast cancer |
| Cancer cells | Hepatocyte growth factor receptor (HGFR) | Anti-HGFR antibody | Colorectal cancer |
| Cancer cells | c-met | Anti-c-met antibody | Gastric and colon cancers, hepatomas, ovarian cancer, skin cancer |
| Large granular lymphocyte (LGL) leukaemia cells | Apoptosis related factors: Fas FasL | Anti-CD95 (Fas) antibody | Leukaemia, prostate cancer |
| Cancer cells | Non-receptor protein tyrosine kinase V-Src and C-Src | Anti c-src-polyclonal antibody | Metastatic colorectal cancer, and late stage breast cancer |
| Cancer cell | CAR (coxsackie adenovirus cell-surface receptor) | Onyx-015 adenovirus | Lung, ovarian, other cancers |
| Cancer cell | Epidermal growth factor receptor (EGFR) | Molecule 225 antibody | Cancer |
| Cancer cells | D6 antigen | Anti-D6 antibody | Vascular tumours including Kaposi's sarcoma |
| Cancer cells | 2C4 antigen | Anti-2C4 antibody | Breast, prostate, other cancers |
| Cancer cells | Cytokeratin epithelial marker and/or telomerase reverse transcriptase | S5A10-2 antibody | Non-small cell lung cancer |
| Cancer cells | Carcinoembryonic antigen (CEA) | MFE-23 scFv of anti-CEA antibody | Colorectal cancer |
| Cancer cells | Proliferating cell nuclear antigen (PCNA) | Anti-PCNA antibody | Breast cancer |
| Cancer cells | Neu 3, a membrane associated sialidase | Anti-neu 3 sialidase antibody | Colon cancer |
| Cancer cells | P13KC2 beta (cancer cell signal mediator) | Anti-P13KC2beta antibody | Lung cancer |
| Cancer cells | Guanylyl cyclase-C (GC-C) receptor | Anti-GC-C antibody | Esophageal or gastric cancer |
| Cancer cells | Transforming growth factor beta (TGFB) receptor | Anti-TGFB antibody | Breast cancer |
| Cancer cells | Platelet derived growth factor receptor (PDGFR) PDGFR-A (alpha) PDGFR-B (beta) | Anti-PDGF-A antibody Anti-PDGF-B antibody | Lung cancer Bone cancer |
| Cancer cells and blood vessels | Vascular endothelial growth factors VEGFR angiopoietin | Tie1 Tie2 | Cancer Cancer |
| Cancer cells | Mucin family of receptors | Anti-MUC-1 antibody, 12E antibody 3D antibody A5 antibody | Colorectal and ovarian carcinomas |
| Cancer cells | TAG-72 | B72.3 antibody | Breast and lung cancers |
| Cancer cells | Human milk fat globule receptor | NCL-HMFG1 and NCL-HMFG2 antibodies | Breast, lung, colon, and prostate cancers |
| Methionine synthase and L-methylmalonyl-CoA mutase | Cobalamin receptor | B12 (riboflavin, and variants) cobalamin and variants, such as adenosylcobalamin transcobalamin | Breast, lung, colon, sarcomatous thyroid or central nervous system malignancies cancer |
| Cancer cells | Glioma chloride channel | Scorpion toxin-chlorotoxin and chlorotoxin-like molecules | Gliomas |

TABLE 1-continued

Bioprobe Systems and Indications

| BIOPROBE SYSTEM | | | |
|---|---|---|---|
| TARGET | MARKER | LIGAND | INDICATION |
| Cancer cells | 40 kD glycoprotein antigen | NR-LU-10 antibody | Small cell lung cancer |
| CNS cells and tissue | Brain-specific chondroitin sulphate proteoglycan Brain enriched hyaluronan binding protein (BEHAB- aka brevican | Anti-BEHAB antibody | Gliomas |
| Cancer cells | Catenins Alpha catenin Beta catenin | Anti-alpha catenin antibody Anti-beta catenin antibody | Colorectal carcinoma, non-small cell lung cancer Breast cancer |
| | Gamma catenin | Anti-gamma catenin antibody | Thyroid cancer |
| Cancer cells | Interleukin (IL) receptors IL13 receptor | IL13-PE38 antibody | Kidney, brain, breast, and head and neck cancers, and Kaposi's sarcoma |
| Cancer cells | Mesothelin receptor | Anti-mesothelin antibody, and SS1 (dsFv) variant | Mesotheliomas Ovarian cancer and mesotheliomas |
| Cancer cells | CD44 surface adhesion molecule | Anti-CD44 antibody | Prostate cancer |
| Cancer cells | EGFRvIII | Ua30:2 antibody L8A4 antibody DH8.3 antibody 81C6 antibody | Brain, colorectal, pancreatic, billary, liver cancers and soft tissue sarcomas. |
| Receptor tyrosine kinases FLT1 | Vascular endothelial growth factor (VEGF) and VEGFB | Anti-FLT1 antibody | Atherosclerotic plaques |
| Smooth muscle cells in the lumen of blood vessels | Basic fibroblast growth factor receptor (bFGFR) | Anti-bFGF antibody | Restenosis |
| Vulnerable plaque | Oxidized low density lipoprotein (OxLDL) | Oxidation-specific antibodies (Ox-AB) MDA-2 antibody | Atherosclerosis and vascular disease |
| Vulnerable plaque | Malondialdehyde-modified LDL (MDA-LDL) | IK17 antibody | Atherosclerosis and vascular disease |
| M. Tuberculosis bacilli | APA-antigen | Anti-APA antibody | Tuberculosis |
| Retrovirus infected cells | TGFA (alpha) | Anti-TGFA antibody | HIV |
| Leukocytes | Alpha4 subunit of alpha4beta1-integrin (VLA-4) and alpha4beta7-integrin | Antegren | Multiple sclerosis |
| Receptor tyrosine kinases FLT1 | Vascular endothelial growth factor (VEGF) and VEGFB | Anti-FLT1 antibody | Autoimmune joint destruction (arthritis, lupus, etc) |
| Plasmodium falciparum | Apical membrane antigen-1 (AMA-1) | Anti-AMA-1 antibody | Malaria |

The methods of the present invention may be used to treat a variety of indications which include, but are not limited to, cancer of any type, such as bone marrow, lung, vascular, neuro, colon, ovarian, breast and prostate cancer, diseases of the immune system, such as AIDS and autoimmune conditions, and pathogen-borne diseases, such as HIV, malaria and tuberculosis, and undesirable matter, such as adverse angiogenesis, amyloidosis, restenosis, vascular conditions, obesity, toxins and other abnormal cell or tissue growth. The bioprobe systems described herein may be used to treat other indications than the associated indications listed in Table 1.

Targets, markers and ligands for use in the present invention include, but not limited to, those disclosed hereinabove, those listed in Table 1, as well as those disclosed in related patent applications having U.S. Ser. Nos. 10/176,950 and 10/200,082, which are incorporated herein by reference.

Administration of Bioprobes

A method of administering the bioprobes 100 to the desired area for treatment and the dosage may depend upon, but is not limited to, the type and location of the diseased material. The size range of the bioprobes 100 allows for microfiltration for sterilization. An administration method may be, for example, wash, lavage, as a rinse with sponge, or other surgical cloth as a perisurgical administration technique. Other methods of administration may include intravascular injection, intravenous injection, intraperitoneal injection, subcutaneous injection, and intramuscular injection. The bioprobes 100 may be formulated in an injectable format (suspension, emulsion) in a medium such as, for example, water, saline, Ringer's solution, dextrose, albumin solution, and oils. The bioprobes 100 may also be administered to the patient through topical application via a salve or lotion, transdermally through a patch, orally ingested as a pill or capsule or suspended in a liquid or rectally inserted in suppository form. Bioprobes 100 may also be suspended in an aerosol or pre-aerosol formulation suitable for inhalation via the mouth or nose. Once administered to the patient, delivery of the bioprobes 100 to the target site may be assisted by an applied static magnetic field due to the magnetic nature of the bioprobes 100. Assisted delivery may depend on the location of the targeted cell. The bioprobes may also be delivered to the patient utilizing other methods. For example, the bioprobes 100 may be administered to the patient orally, or may be administered rectally.

The Energy Source external beam radiotherapy is used in combination with the targeted thermotherapy methods disclosed herein. If both the targeted thermotherapy and radiotherapy methods are used simultaneously, the AMF system may comprise a separate opening for the beam to enter. Alternatively, the beam may be directed through the patient's opening (patient gantry). Intraoperative irradiation is a technique in which a large dose of external radiation is directed at the tumor and surrounding tissue during surgery.

Gamma rays are produced spontaneously as certain elements (such as radium, uranium, and cobalt 60) release radiation as they decompose or decay. Each element decays at a specific rate and emits energy in the form of gamma rays and other particles. X-rays and gamma rays generally have the same effect on cancer cells.

TABLE 2

Energy Sources for Energizing Bioprobes

| CORRESPONDING SECTION BELOW | ENERGY FORM | ENERGY SOURCE | THERAPEUTIC MECHANISM |
| --- | --- | --- | --- |
| 2.3.1 | Ionizing radiation -- Neutron, alpha, beta, gamma, x-ray | Nuclear reactor, particle accelerators, radioactive materials, cyclotrons, pulsed voltage (above 40 kV) source. | Combination Mechanism -- Damage to genetic material with heat |
| 2.3.2 | AMF | Power Generator/Inductor | Hysteresis (Induction) Heating |
| 2.4 | AMF, Ionizing radiation | | Extracorporeal |

Targeted Thermotherapy in Combination with Radiation Therapy

Radiotherapy, also referred to as radiation therapy, is the treatment of cancer and other diseases utilizing ionizing radiation. Ionizing radiation deposits energy that injures or destroys cells in the area being treated (the "target tissue") by damaging their genetic material, making it impossible for these cells to continue to grow. Although radiation damages both cancer cells and normal cells, the latter are able to repair themselves and function properly. Radiotherapy may be used to treat localized solid tumors, such as cancers of the skin, tongue, larynx, brain, breast, or uterine cervix. It can also be used to treat leukemia and lymphoma (cancers of the blood-forming cells and lymphatic system, respectively). In one embodiment of the present invention, radiotherapy or radiation therapy is used in combination with the targeted thermotherapy methods disclosed herein. Radiotherapy is applied at least once prior to, or at least partly during, or at least once after targeted therapy administration, or any combination thereof.

One type of radiation therapy commonly used involves x-rays or gamma rays. X-rays were the first form of photon radiation to be used to treat cancer. Depending on the amount of energy they possess, the rays can be used to destroy cancer cells on the surface of or deeper in the body. The higher the energy of the x-ray beam, the deeper the penetration of the x-rays into the target tissue. Linear accelerators and betatrons are machines that produce x-rays of increasingly greater energy. The use of machines to focus radiation (such as x-rays) on a cancer site is referred to as external beam radiotherapy. These beams are shielded from the outside world and special shielding is used for "focusing" these beams onto defined body areas. In one embodiment of the invention, Another investigational approach is particle beam radiation therapy. This type of therapy uses fast-moving subatomic particles to treat localized cancers. Particle accelerators are used to produce and accelerate the particles required for this procedure. Some particles (neutrons, pions, and heavy ions) deposit more energy than x-rays or gamma rays along the path they take through tissue, thus causing more damage to the cells they contact. This type of radiation is often referred to as high linear energy transfer (high LET) radiation. In one embodiment of the invention, high LET therapy is used in combination with the targeted thermotherapy methods disclosed herein.

Another technique for delivering radiation to cancer cells is to place radioactive implants directly in a tumor or in a body cavity. This is referred to as internal radiotherapy. (Brachytherapy, interstitial irradiation, and intracavitary irradiation are types of internal radiotherapy.) During this treatment, the radiation dose is concentrated in a small area, and the procedure may require the patient to stay in the hospital for a few days. In one embodiment of the invention, internal radiotherapy is used in combination with the targeted thermotherapy methods disclosed herein. The implant comprises a material that heats during the targeted therapy administration by eddy current or hysteretic heating, or comprises a material that does not heat under AMF exposure, such as plastic, ceramic, glass, or transplanted human tissue.

In one embodiment of the invention, radiolabled antibodies deliver doses of radiation directly to the cancer site (radioimmunotherapy) in combination with targeted thermotherapy. At least one radioisotope 140 is attached to bioprobe 100, as illustrated in FIG. 1. Such a bioprobe can be a dual therapy bioprobe. Once injected into the body, the antibodies actively seek out the cancer cells, which are destroyed by the cell-killing (cytotoxic) action of the radiation.

Examples of radioisotopes suitable for use herein are:

Molybdenum-99: Used as the 'parent' in a generator to produce technetium-99m, the most widely used isotope in nuclear medicine.

Technetium-99m: Used particularly for imaging the skeleton and heart muscle, and for imaging the brain, thyroid, lungs (perfusion and ventilation), liver, spleen, kidney (structure and filtration rate), gall bladder, bone marrow, salivary and lacrimal glands, heart blood pool, infection and numerous specialized medical studies.

Chromium-51: Used for labeling red blood cells and quantifying gastro-intestinal protein loss.

Cobalt-60: Used for external beam radiotherapy.

Copper-64: Used for studying genetic diseases affecting copper metabolism, such as Wilson's and Menke's diseases.

Dysprosium-165: Used as an aggregated hydroxide for synovectomy treatment of arthritis.

Ytterbium-169: Used for cerebrospinal fluid studies in the brain.

Iodine-125: Used in cancer brachytherapy (prostate and brain), also used for diagnostic evaluation of the kidney filtration rate and for diagnosing deep vein thrombosis in the leg. It is also widely used in radioimmuno assays to show the presence of hormones in small quantities.

Iodine-131: Widely used in treating thyroid cancer and in imaging the thyroid; also used in the diagnosis of abnormal liver function, renal (kidney) blood flow and urinary tract obstruction. Although it is a strong gamma emitter, it is used for beta therapy.

Iridium-192: Supplied in wire form for use as an internal radiotherapy source for cancer treatment.

Iron-59: Used for studying iron metabolism in the spleen.

Phosphorus-32: Used in the treatment of polycythemia vera (excess red blood cells). It is a beta emitter.

Potassium-42: Used for the determination of exchangeable potassium in coronary blood flow.

Rhenium-188 (derived from Tungsten-188): Used for beta irradiating coronary arteries from an angioplasty balloon.

Samarium-153: Very effective in relieving the pain of secondary cancers lodged in the bone. It is commercially available as Quadramet™. Also, it is very effective for prostate and breast cancer. It is a beta emitter.

Selenium-75: Used in the form of seleno-methionine to study the production of digestive enzymes.

Sodium-24: Used for studies of electrolytes within the body.

Strontium-89: Very effective in reducing the pain of prostate cancer. Beta emitter.

Xenon-133, Xenon-127: Used for pulmonary (lung) ventilation studies.

Yttrium-90: Used for cancer therapy and as silicate colloid for the treatment of arthritis in larger joints. It is a beta emitter.

Radiation therapy in combination with targeted thermotherapy may also be used alone, or in combination with chemotherapy, surgery or both.

Figure 3:
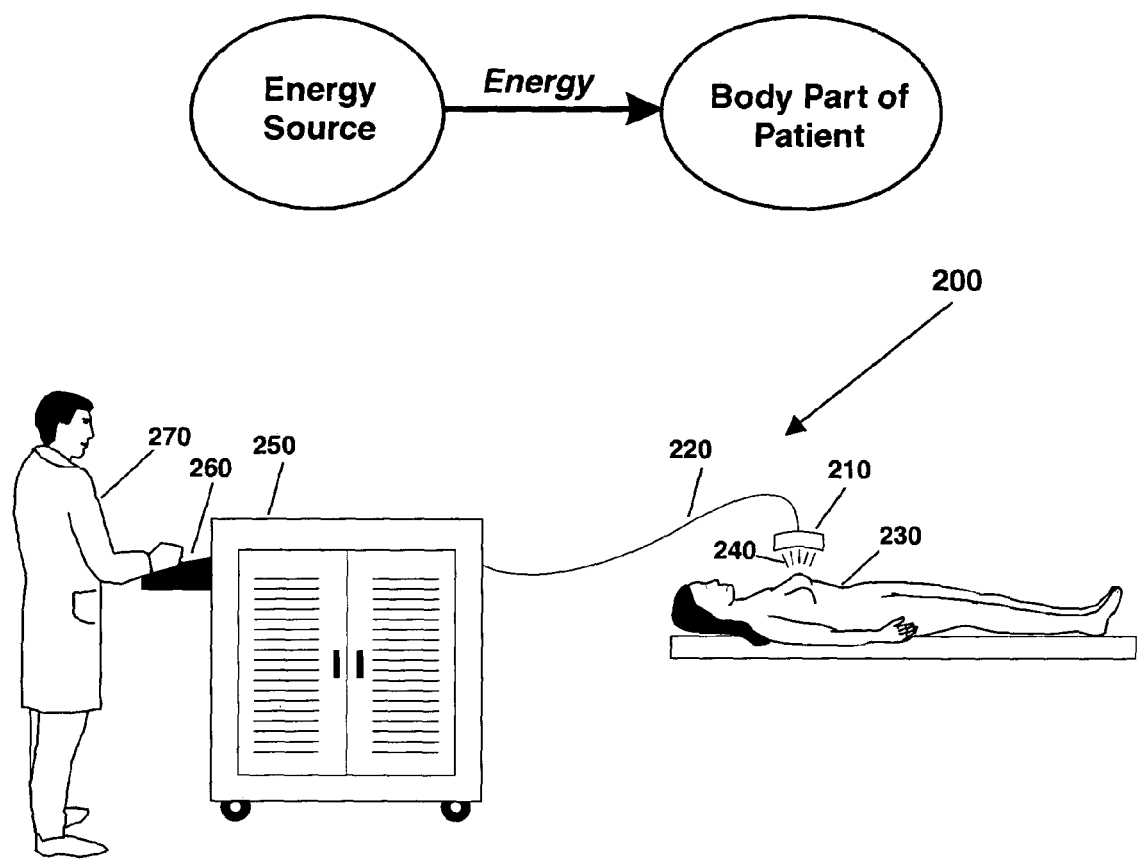
FIG. 3 schematically illustrates a therapy system, according to an embodiment of the present invention.

The energy source for use in the present invention includes any device that is able to provide AMF at the appropriate frequency, or microwave at the appropriate frequency to the bioprobe so that it can convert that energy to heat. In one embodiment of the present invention, energy is delivered to the bioprobe, which then transmits the heat to the targeted cell(s) and cells or tissue that surround the targeted cell(s). In another embodiment, an additional energy source is used in combination AMF or Microware for converting a bioprobe into a source of ionising radiation (neutron, alpha, beta, gamma, etc.). FIG. 3 schematically illustrates an energy source that transmits energy to a subject's body or a body part. Some exemplary energy forms and energy sources useful herein are listed in Table 2. The different forms of energy, for example AMF, or a combination comprising AMF, may be created using a variety of mechanisms, such as those listed in Table 2. The table also lists those sections of the following descriptions that are pertinent to the different energy forms and therapeutic mechanisms.

In general, as illustrated in FIG. 3, operator 270 controls an energy generating device 250, for example via a console 260, which delivers energy, for example via a cable 220, to an energy source 210. Energy source 210 transmits energy to the bioprobe's susceptor to heat or otherwise affect the targeted cell, and cells or tissue that surround the bioprobe in a subject 230.

It will be appreciated that the AMF energy sources described herein may also be used for heating other types of bioprobes, for example, the bioprobes disclosed in patent applications having U.S. Ser. Nos. 10/176,950 and 10/200, 082. It will further be appreciated that the energy sources disclosed in patent applications having U.S. Ser. Nos. 10/176, 950 and 10/200,082 may also be used for heating the bioprobes of the present invention.

Alternating Magnetic Field (AMF) Heating

In some embodiments of the present invention, AMF energy may be used with a bioprobe to produce therapeutic heating through hysteresis loss mechanisms in the magnetic nanoparticles of the bioprobes.

Figure 4:
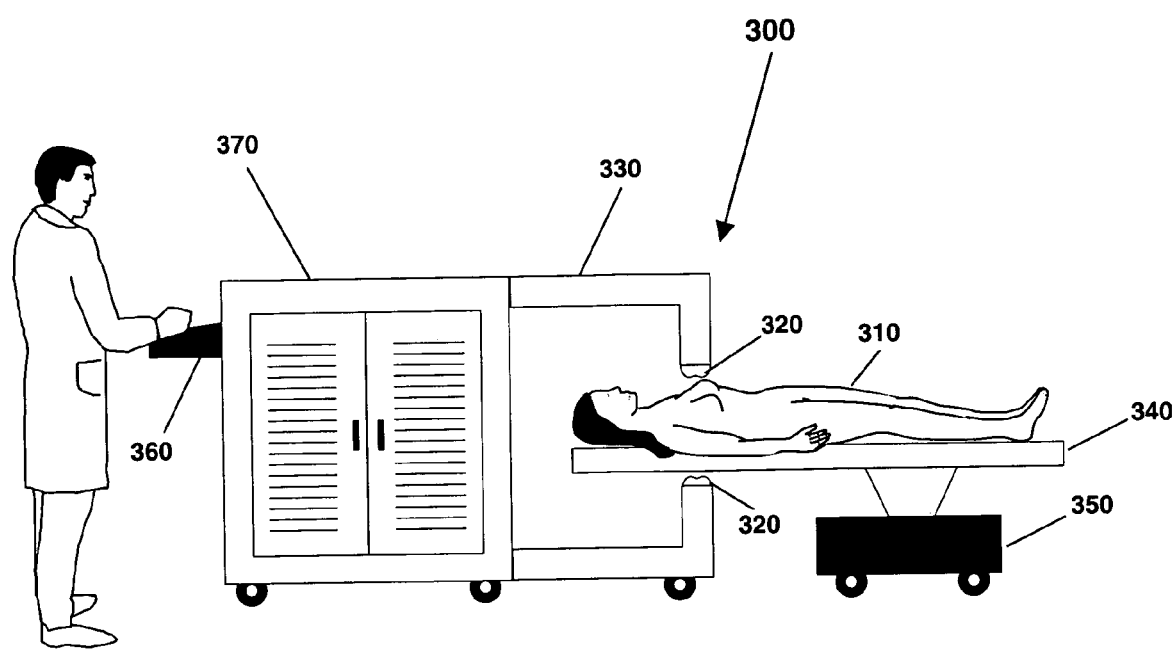
FIG. 4 schematically illustrates a therapy system, according to an embodiment of the present invention.

In one embodiment of the present invention, as illustrated in FIG. 4, the therapeutic system 300 comprises an AMF generator, which is located for example within a cabinet 370, designed to produce an AMF that may be guided to a specific location within a subject 310 by a magnetic circuit 330. Subject 310 is placed upon an X-Y horizontal and vertical axis positioning bed 340. Positioning bed 340 can be positioned horizontally and vertically via a bed controller 350. The AMF generator produces an AMF in magnetic circuit 330 that exits magnetic circuit 330 at one pole face 320, passing through the air gap and the desired treatment area of subject 310, and reenters magnetic circuit 330 through the opposing pole face 320, thus completing the circuit. An operator or medical technician preferably controls and monitors the AMF characteristics and bed positioning via a control panel 360. When the AMF is generated by an RF generator, the frequency of the AMF is preferably in the range of about 80 kHz to about 800 kHz.

Figure 5:
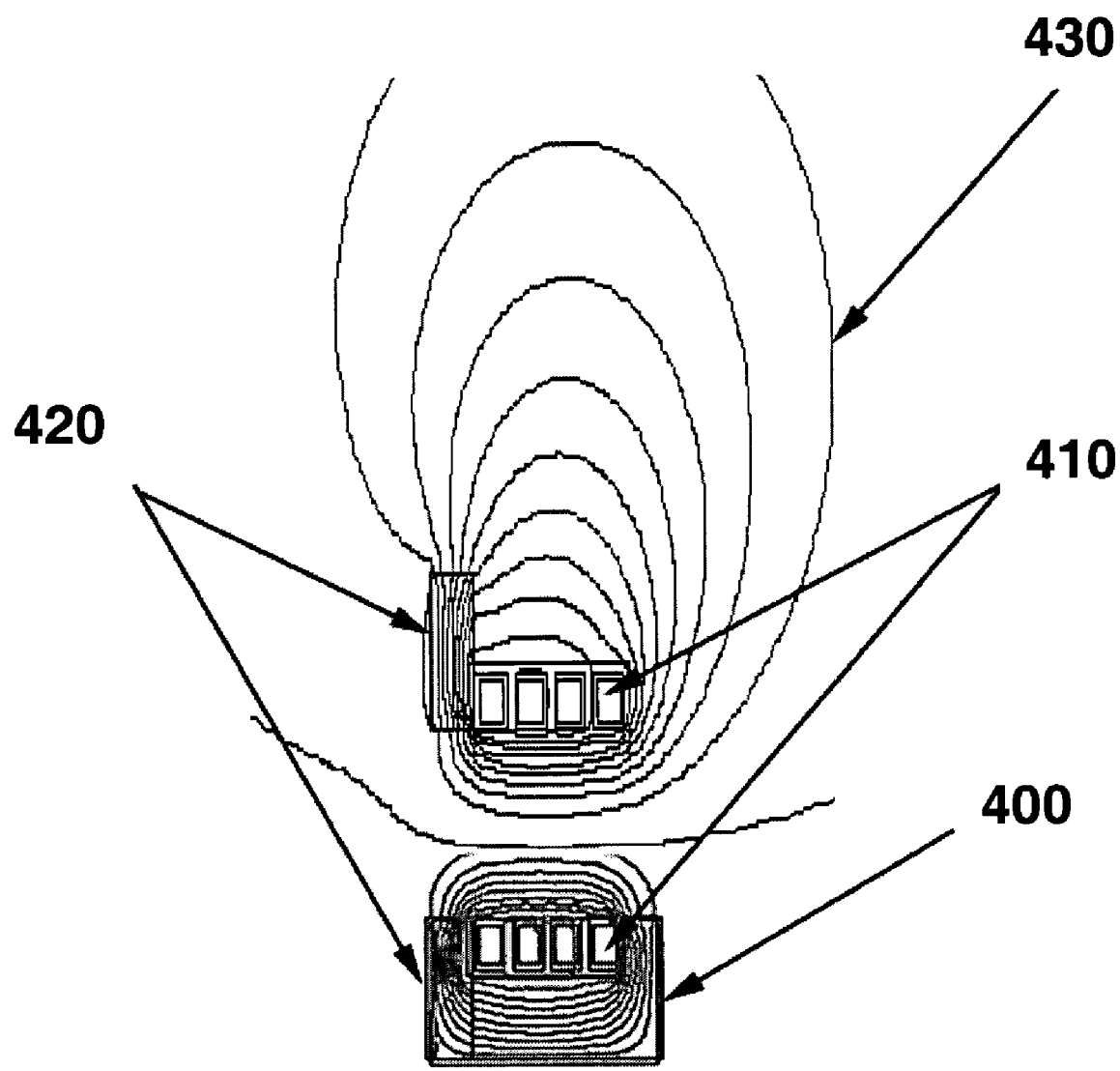
FIG. 5 schematically illustrates a cross-sectional view of a solenoid coil used as an AMF energy source.

Other approaches may be used to generate the AMF, and may provide a focused and/or a homogeneous field. In one embodiment, a magnetic solenoid coil 410 may be particularly useful for heating bioprobes in tissue having high length to diameter ratios, such as human limbs or small animals. This is illustrated in FIG. 5, which shows a cross-sectional view of the magnetic solenoid coil 410. The coil 410 comprises a circular, doughnut shaped ring 420 of low reluctance magnetic material, which may be specifically formulated for magnetic cores operating at a desired frequency, for example about 150 kHz. One example of such a low reluctance magnetic material is Fluxtrol™ (commercially available from Fluxtrol Manufacturing Inc., Auburn Hills, Mich., USA).

A magnetic flux focusing bar 400, fabricated from a length of a low reluctance magnetic material may be positioned so as to surround about 25% of the circumference of the outer diameter of solenoid coil 410 and to stretch from the ring 420 to the opposite end of solenoid coil 410. The magnetic flux focusing bar 400 may be fabricated from the same material as the ring 420, or from a different material. For example, the bar 400 may be fabricated from Ferrotron™ (commercially available from Fluxtrol Manufacturing Inc.).

The ring 420 and focusing bar 400 direct a magnetic flux 430 in a pattern that exposes a reduced cross-section of a human or animal body or body part to the magnetic field. Because eddy current heating is proportional to the square of the cross-section of the exposed tissue in magnetic flux 430, it is advantageous to reduce the size of the exposed cross-section. This approach allows for higher magnetic field strengths for application to the subject with reduced eddy current heating. In addition, circular doughnut shaped ring 420 and focusing bar 400 cause the field strength to drop off significantly outside of solenoid coil 400. Magnetic solenoid coil 410 focuses the AMF while protecting the non-targeted parts of the subject, such as the head and vital organs.

The magnetic susceptors for use herein typically are susceptible to AMF energy supplied by the energy source, and heat when exposed to AMF energy; are biocompatible; and have surfaces that have (or can be modified to have) functional groups to which ligands can be chemically or physically attached. In one embodiment of the present invention, a bioprobe having a magnetic nanoparticle core is surrounded by a biocompatible coating material. There are many possible combinations of core-coating materials. For example, gold as a coating material is particularly advantageous because it forms a protective coating to prevent a chemical change, such as oxidation, in the core material, while being biocompatible. A gold coating can also be chemically modified to include groups for ligand linking. Further, gold may serve as a good conductor for enhancing eddy current heating associated with AMF heating.

Types of magnetic susceptor cores that require a protective coating include iron, cobalt, other magnetic metals, and their less stable oxides. An example of the latter is magnetite, $Fe_3O_4$, which will undergo further oxidation to form maghemite ($\gamma$-$Fe_2O_3$) and eventually/or hematite ($\alpha$-$Fe_2O_3$). Iron and cobalt, for example, are susceptible to chemical changes, such as oxidation, and possess magnetic properties that are significantly changed due to oxidation. The use of a protective coating is especially preferred in embodiments where the core material may pose a toxic risk to humans and animals in vivo. Thus, the use of a gold coating material is particularly preferred to protect the core material from chemical attack, and to protect the subject from toxic effects of the core material.

In one embodiment of the present invention, the gold coating is chemically modified via thiol chemistry such that a chemical link is formed between the gold surface and a suitable ligand. For example, an organic thiol moiety can be attached to the gold, followed by linking the ligand to the organic thiol moiety using at least one silane, carboxyl, amine, or hydroxyl group, or a combination thereof. Other chemical methods for modifying the surface of the coating material may also be utilized.

In another embodiment, nitrogen-doped Mn clusters are used as magnetic susceptors. These nitrogen-doped Mn clusters, such as MnN and $Mn_xN_y$, where x and y are nonzero numbers, are ferromagnetic and comprise large magnetic moments. Calculations based on density-functional theory show that the stability and magnetic properties of small Mn clusters can be fundamentally altered by the presence of nitrogen. Not only are their binding energies substantially enhanced, but also the coupling between the magnetic moments at Mn sites remains ferromagnetic regardless of their size or shape.

In another embodiment, $Nd_{1-x}CaFeO_3$ is used as a magnetic susceptor. The spontaneous magnetization of the weak ferromagnetism decreases with increasing Ca content or increasing particle size.

Other materials, such as aggregates of superparamagnetic grains of $CO_{36}C_{64}$, $Bi_3Fe_5O_{12}$, $BaFe_{12}O_{19}$, NiFe, CoNiFe, Co—$Fe_3O_4$, and FePt—Ag, where the collective state of the aggregate induces magnetic blocking, may also be used as susceptors in the present invention.

Microwave Resonance Heating

It is well known that atoms, molecules, and crystals possess resonance frequencies at which energy absorption is effectively achieved. In general, resonance heating offers significant advantages because the targeted material absorbs large quantities of energy from a relatively low power source. Thus, non-targeted materials, including body tissue, the resonant frequency of which differs from that of the targeted material, do not heat to the same extent. Accordingly, materials may be selected to take advantage of a particular resonant frequency in the electromagnetic energy spectrum. A susceptor material may be selected such that the internal chemical bonds of the material may resonate at a particular frequency.

Resonance heating can also be achieved by exploiting interactions of the microwave energy with materials that possess magnetic, electrical, or electric dipole structures on the atomic, molecular, or macroscopic length scales. In addition to the direct modes of heating described above, resonance heating may be used indirectly. In one embodiment of the present invention, materials for use as bioprobes are selected such that they possess magnetic or electric properties that will induce a shift in the resonance frequency of the tissue to which they become attached. Thus, the molecules of the tissue in close proximity to the bioprobes will heat preferentially in an applied energy field tuned to the appropriate frequency.

The energy can be applied to a targeted cell, targeted tissue, to the entire body, extracorporeally (outside of the subject's body), or in any combination thereof.

Extracorporeal Therapy

In one embodiment of the present invention, a subject is treated via extracorporeal therapy. The bioprobes may be used to lyse, denature, or otherwise damage the disease material by removing material from the subject, exposing the material to an energy source, and returning the material to the body. The bioprobes may be introduced into the subject's body or body part, and then removed from the subject along with the material that is being extracted. The bioprobes may be separated from the material that is extracted after the treatment. In another embodiment, the bioprobes are introduced to the extracted material while the extracted material is outside of the subject's body or body part. For example, where the extracted material is the subject's blood, the bioprobes may be introduced to the vascular circulating system or into the blood circulating outside of the body, prior to exposure to an energy source.

In embodiments where the bioprobe/target complexes that are carried primarily in the blood serum or blood plasma are targeted, the blood serum or blood plasma may be separated extracorporeally from the other blood components, exposed to an energy source so as to destroy or inactivate the target, and recombined with the other blood components prior to returning the blood to the subject's body. The bioprobes may be introduced into the vascular circulating system, the blood circulating outside of the body, or the blood serum or blood plasma after it is separated.

In another embodiment, the bioprobes may be contained in a vessel or column through which the blood circulating outside of the body or the blood serum or blood plasma flows. The vessel or column may be exposed to an energy source so as to destroy or inactivate the targeted cells or antigens prior to returning the blood to the subject's body.

The advantages of providing energy to the bioprobes extracorporeally include the ability to heat to higher temperatures and/or heat more rapidly to enhance efficacy while minimizing heating and damage to surrounding body tissue, and the ability to reduce exposure of the body to the energy from the energy source. In embodiments where the bioprobes are introduced into the blood circulating outside of a subject's body, the blood serum, or blood plasma that is extracted from the body, bioprobes need not be directly introduced into the body, and higher concentrations of bioprobes can be introduced to target. Further, the portion of the subject that is being treated extracorporeally can be cooled externally, using a number of applicable methods, while energy is provided to the bioprobes without mitigating the therapeutic effect. In addition, the cooling may take place before, and/or after the administration of energy.

The treated bioprobes and the associated targets need not be returned to the subject's body. For example, if the bioprobes and the associated targets are contained in blood extracted from a subject, the treated bioprobes and the associated targets may be separated from the blood prior to returning the blood to the subject's body. In embodiments where the bioprobes contain a magnetic component, the bodily fluids containing the bioprobes and associated targets are passed through a magnetic field gradient in order to separate the bioprobes and the associated targets from the extracted bodily materials. In doing so, the amount of susceptors and treated disease material returned to the subject's body is reduced.

In another embodiment of extracorporeal treatment, the tissue selected for heating is completely or partially removed from a subject's body, e.g., during an open surgical procedure. The tissue can remain connected to the body or can be dissected and reattached after the therapy. In yet another embodiment, the tissue is removed from the body or body part of one donor subject and transplanted to that of a recipient subject after the therapy.

While the above description of the invention has been presented in terms of a human subject, it is appreciated that the invention may also be applicable to treating other subjects, such as mammals, cadavers and the like.

As noted above, the present invention is applicable to thermotherapeutic compositions for treating disease material, and methods of targeted therapy utilizing such compositions. The present invention should not be considered limited to the particular embodiments described above, but rather should be understood to cover all aspects of the invention as fairly set out in the attached claims. Various modifications, equivalent processes, as well as numerous structures to which the present invention may be applicable will be readily apparent to those skilled in the art to which the present invention is directed upon review of the present specification. The claims are intended to cover such modifications and devices.

I claim:

1. A magnetic composition, comprising:
   a) a magnetic nanoparticle that comprises at least one stable single magnetic domain grain that heats when subjected to an alternating magnetic field with frequency in the range of from about 80 kHz to 800 kHz, amplitude in the range of from about 7.98 kA/m and 104 kA/m, and at a temperature in the range of from about 270 to 380 K; and
   b) a coating.

2. A magnetic composition according to claim 1, wherein the coating comprises dextran.

3. A magnetic composition according to claim 1, further comprising a radio isotope, potential radioactive isotope, a chemotherapeutic agent, or any combination thereof.

4. A magnetic composition according to claim 3, wherein the radioactive isotope is iodine-131, cobalt-60, iridium-192, yttrium-90, strontium-89, samarium-153, rhenium-186, technetium-99m, or any combination thereof.

5. A magnetic composition according to claim 3, wherein the potentially radioactive isotope is an isotope possessing a high absorption cross-section to neutrons, protons, electrons, or high energy photons.

6. A magnetic composition according to claim 5, wherein the potentially radioactive isotope is an isotope possessing a high absorption cross-section to neutrons, and is one of boron-10, a lanthanide such as samarium-149, gadolinium-57, and gadolinium-55 or any combination thereof.

7. A magnetic composition according to claim 6, wherein the desired treatment area is exposed to neutrons, protons, electrons, or high energy photons to activate the potentially radioactive isotope in combination with AMF thermotherapy.

8. A magnetic composition according to claim 3, wherein the chemotherapeutic agent is one of doxorubicin, cisplatin, or any combination thereof.

9. A magnetic composition according to claim 1, wherein the composition further comprises a ligand.

10. A magnetic composition, comprising:
    a) a magnetic nanoparticle that comprises either i) an aggregate of superparamagnetic grains that exhibits a collective magnetic state such that it is apparently blocked when subjected to an alternating magnetic field with frequency in the range of from about 80 kHz to 800 kHz, amplitude in the range of from about 7.98 kA/m and 104 kA/m, and at a temperature in the range of from about 270 to 380 K, or ii) an aggregate of stable single magnetic domain grains and superparamagnetic grains, that exhibits a collective magnetic state such that characteristic relaxation time of the superparamagnetic grains is increased, and the aggregate is apparently blocked when subjected to an alternating magnetic held with frequency in the range of from about 80 kHz to 800 kHz, amplitude in the range of from about 7.98 kA/m and 104 kA/m, and at a temperature in the range of from about 270 to 380 K; and
    b) a coating.

11. A magnetic composition according to claim 10, wherein the coating comprises dextran.

12. A magnetic composition according to claim 11, further comprising a radio isotope, potential radioactive isotope, a chemotherapeutic agent, or any combination thereof.

13. A magnetic composition according to claim 12, wherein the radioactive isotope is iodine-131, cobalt-60, iridium-192, yttrium-90, strontium-89, samarium-153, rhenium-186, technetium-99m, or any combination thereof.

14. A magnetic composition according to claim 12, wherein the potentially radioactive isotope is an isotope possessing a high absorption, cross-section to neutrons, protons, electrons, or high energy photons.

15. A magnetic composition according to claim 14, wherein the potentially radioactive isotope is an isotope possessing has a high absorption cross-section to neutrons, and is one of boron-10, a lanthanide such as samarium-149, gadolinium-157, and gadolinium 155 or any combination thereof.

16. A magnetic composition according to claim 15, wherein the desired treatment area is exposed to neutrons, protons, electrons, or high energy photons to activate the potentially radioactive isotope in combination with AMF thermotherapy.

17. A magnetic composition according, to claim 12, wherein the chemotherapeutic agent is one of doxorubicin, cisplatin, or any combination thereof.

18. A method for treating a patient, comprising:
  a) administering the magnetic composition of claim 10 to at least a portion, of a patient; and
  b) applying an alternating magnetic field (AMF) to the magnetic composition combined with the predetermined target to inductively heat the magnetic material.

19. A method according to claim 18, wherein the magnetic composition further comprises a radio isotope, potential radioactive isotope, a chemotherapeutic agent, or any combination thereof.

20. A method according to claim 18, wherein the AMF is pulsed.

21. A method according to claim 18, wherein the administering utilizes a method that is intraperitoneal injection, intravascular injection, intramuscular injection, subcutaneous injection, topical, inhalation, ingestion, rectal insertion, wash, lavage or rinse perisurgically, extracorporeal or any combination thereof.

22. A method according to claim 18, wherein the magnetic composition of claim 10 is administered directly to the diseased tissue.

23. A magnetic composition according to claim 18, wherein the composition further comprises a ligand specific to a predetermined target in the patient.

24. A method according to claim 23, wherein the target is associated with a cancer, a disease of the subject's vascular system, a disease-causing pathogen, multiple sclerosis, or non-cancerous disease material.

25. A method according to claim 24, wherein the target associated with a cancer comprises a marker, and wherein the marker is a) a member of vascular endothelial growth factor receptor (VEGFR) family; b) a member of carcinoembryonic antigen (CEA) family; e) unglycosylated DF3 antigen; d) a member of epidermal growth factor receptor (EGFR) family; e) a cellular adhesion molecule; f) a matrix metalloproteinase; g) a glycoprotein antigen; h) an antigen; i) a prostate specific membrane antigen (PSMA); j) a small cell lung carcinoma antigen (SCLCA); k) a hormone receptor; l) a tumor suppressor gene antigen; in) a cell cycle regulator antigen; n) an oncogene antigen; o) an oncogene ret antigen; p) a proliferation marker; q) a malignant transformation related factor; r) an apoptosis-related factor; s) a human carcinoma antigen; t) an integrin; u) a kallikrein; v) a placental growth factor receptor (PGFR); w) an adenovirus-cell surface receptor; x) a hepatocyte growth factor receptor (HCFR); y) a tyrosine kinase; z) a cytokeratin epithelial marker; aa) a proliferating cell nuclear antigen (PCNA); bb) a membrane associated sialidase; cc) a cancer cell signal mediator; dd) a cyclase-C receptor; ee) a transforming growth factor receptor (TGFR); ff) a platelet derived growth factor receptor (PDGFR); gg) a cobalamin receptor; hh) a glioma channel; ii) a brain specific chondroitin sulphate proteoglycan; jj) a catenin; kk) a member of MUC-type mucin family receptors; ll) a member of cluster designation/differentiation (CD) antigen family; mm) a protein antigen; nn) a cytokine receptor; oo) a mesothelin receptor; or pp) any combination of a) through oo).

26. A method according to claim 25, wherein the ligand to the marker is a) a polyclonal anti body; b) a monoclonal anti body; c) a chimeric antibody; d) a humanized antibody; e) a human antibody; f) a recombinant antibody; g) a bispecific antibody; h) an antibody fragment; i) a recombinant single chain antibody fragment; or j) any combination of a) through i).

27. A method according to claim 26, wherein the ligand is an antibody to marker human milk fat globule receptor (HMFGR), a variant of antibody to marker HMFGR, or any combination thereof.

28. A method according to claim 26, wherein the ligand is an antibody to marker EGFRvIII, a variant of antibody to marker EGFRvIII, or any combination thereof.

29. A method according to claim 26, wherein the ligand is an antibody to marker OxLDL, a variant of antibody to marker OxLDL, or any combination thereof.

30. A method according to claim 26, wherein the ligand is an antibody to marker MDA-LDL, a variant of antibody to marker MDA-LDL, or raw combination thereof.

31. A method for imaging a patient, comprising:
  a) administering the magnetic composition of claim 10 to at least a portion of a patient; and
  b) applying a magnetic field to the magnetic composition to enhance the image of the portion of the patient containing the magnetic material.

32. A method according to claim 31, wherein the magnetic composition of claim 9 is administered directly to the target tissue.

33. A magnetic composition according to claim 31, wherein the composition further comprises a ligand specific to a predetermined target in the patient.

34. A method according to claim 31, wherein the magnetic composition further comprises a radio isotope or a potential radioactive isotope or any combination thereof to enhance the contrast of the target tissue.

35. A magnetic composition according to claim 10, wherein the composition further comprises a ligand specific to a predetermined target in the patient.

36. A method for treating a patient, comprising:
  a) administering the magnetic composition of claim 1 to at least a portion of a patient; and
  b) applying an alternating magnetic field (AMF) to the magnetic composition to inductively heat the material.

37. A method according to claim 36, wherein the AMF is pulsed.

38. A method according to claim 37, wherein the AMF 'on' pulse times are in the range of from about 0.1 seconds to about 1200 seconds, and the 'off' pulse times are in the range of from about 0.1 seconds to about 1200 seconds.

39. A method according to claim 36, wherein the administering utilizes a method that is intraperitoneal injection, intravascular injection, intramuscular injection, subcutaneous injection, topical, inhalation, ingestion, rectal insertion, wash, lavage or subcutaneous injection rinse perisurgically, extracorporeal, or any combination thereof.

40. A method according to claim 39, wherein the administering utilizes a method that is extracorporeal and at least a portion of the subject is extracted from the subject's body prior to extracorporeal administration of AMF, and wherein the extracted portion is returned to the subject's body or is transplanted to a recipient's body after the administration of AMF.

41. A method according to claim 40, wherein the extracted portion of the subject is cooled before, during or after the administration of AMF.

42. A method according to claim 40, wherein the magnetic composition is removed from the extracted portion via a magnetic force after the administration of AMF.

43. A method according to claim 36, wherein the magnetic composition of claim 1 is administered, directly to the diseased tissue.

44. A method according to claim 36, wherein the magnetic composition further comprises a ligand specific to a predetermined target in the patient.

45. A method according to claim 44, wherein the target is associated with a cancer, a disease of the subject's vascular system, a disease-causing pathogen, a central nervous system disease, or non-cancerous disease material.

46. A method according to claim 45, wherein the target associated with a cancer comprises a marker, and wherein the marker is a) a member of vascular endothelial growth factor receptor (VEGFR) family; b) a member of carcinoembryonic antigen (CEA) family; c) unglycosylated DF3 antigen; d) a member of epidermal growth factor receptor (EGFR) family; e) a cellular adhesion molecule; f) a matrix metalloproteinase; g) a glycoprotein antigen; h) an antigen; i) a prostate specific membrane antigen (PSMA); j) a small cell lung carcinoma (SCLCA); k) a hormone receptor; l) a tumor suppressor gene antigen; m) a cell cycle regulator antigen; n) an oncogene antigen; o) an oncogene receptor antigen; p) a proliferation marker; q) a malignant transformation related factor; r) an apoptosis-related factor; s) a human carcinoma antigen; t) an integrin; u) a kallikrein; v) a placental growth factor receptor (PGFR); w) an adenovirus-cell surface receptor; x) a hepatocyte growth factor receptor (HGFR); y) a tyrosine kinase; z) a cytokeratin epithelial marker; aa) a proliferating cell nuclear antigen (PCNA); bb) a membrane associated sialidase; cc) a cancer cell signal mediator; dd) a cyclase-C receptor; ee) a transforming growth factor receptor (TGFR); ff) a platelet derived growth factor receptor (PDGFR); gg) a cobalamin receptor; hh) a glioma channel; ii) a brain specific chondroitin sulphate proteoglycan; jj) a catenin; kk) a member of MUC-type mucin family receptors; ll) a member of cluster designation/differentiation (CD) antigen family; mm) a protein antigen; nn) a cytokine receptor; oo) a mesothelin receptor; or pp) any combination of a) through oo).

47. A method according to claim 46, wherein the ligand to the marker is a) a polyclonal antibody; b) a monoclonal antibody; c) a chimeric antibody; d) a humanized antibody; e) a human antibody; f) a recombinant antibody; g) a bispecific antibody; h) an antibody fragment; i) a recombinant single chain antibody fragment; j) any combination of a) through i).

48. A method according to claim 46, wherein the marker epidermal growth factor receptor (EGFR) comprises HER-1, HER-2, HER-3, HER-4, EGFRvIII, or any combination thereof.

49. A method according to claim 47, wherein the ligand is an antibody to marker HER-2, a variant of antibody to marker HER-2, or any combination thereof.

50. A method according to claim 49, wherein the variant of antibody to matter HER-2 is F5 scFv, IDM-1 (MDX-210), or any combination thereof.

51. A method according to claim 47, wherein the ligand is an antibody to marker EGFRvIII, a variant of antibody to marker EGFRvIII, or any combination thereof.

52. A method according to claim 51 wherein the variant of antibody to marker EGFRvIII is Ua30:2, L8A4, DH8.3, 81C6, or any combination thereof.

53. A method according to claim 46, wherein the marker MUC-type mucin family receptors comprises MUC-1, MUC-2, MUC-3, TAG-72, human milk fin globule receptor, or any combination thereof.

54. A method according, to claim 47, wherein the ligand is an antibody to marker MUC-1, a variant of antibody to marker MUC-1, or any combination thereof.

55. A method according to claim 47, wherein the ligand is an antibody to marker TAG-72, a variant of antibody to marker TAG-72, or any combination thereof.

56. A method according to claim 55, wherein the variant of antibody to marker TAG-72 is B72.3.

57. A method according to claim 47, wherein the ligand is an antibody to marker CEA, a variant of antibody to marker CEA, or any combination thereof.

58. A method according to claim 57, wherein the variant of antibody to marker CEA is MFE-23 scFv.

59. A method according, to claim 46, wherein the marker designation/differentiation protein comprises CD44, and wherein CD44 serves as a cellular adhesion molecule.

60. A method according to claim 46, wherein the marker cytokine receptor comprises at least one member of the interleukin (IL) family.

61. A method according to claim 20, wherein the ligand is an antibody to marker IL13, a variant of antibody to marker IL13, or any combination thereof.

62. A method according to claim 46, wherein the marker matrix metalloproteinase comprises matrix metal metalloproteinase 9 (MMP-9).

63. A method according to claim 46, wherein the marker glycoprotein antigen comprises a 43 kD membrane associated glycoprotein antigen, a 40 kD glycoprotein antigen, or any combination thereof.

64. A method according to claim 47, wherein the ligand is an antibody to marker 43 kD glycoprotein associated glycoprotein antigen, a variant of antibody to marker 43 kD membrane associated glycoprotein antigen, or any combination thereof.

65. A method according to claim 64, wherein the variant of antibody to marker 43 kD membrane associated glycoprotein antigen is 323/A3.

66. A method according to claim 47, wherein the ligand is an antibody to marker 40 kD glycoprotein antigen, a variant of antibody to marker 40 kD glycoprotein antigen, or any combination thereof.

67. A method according to claim 66, wherein the variant of antibody to marker 40 kD glycoprotein antigen is NR-LU-10.

68. A method according to claim 46, wherein the marker antigen comprises a vascular endothelial growth factor receptor (VEGFR), integrin αvβ3, a urokinase type plasminogen activator receptor (uPAR), a plasminogen activator inhibitor 1 (PAI-1), VEGFR 2 (KDR/Flk-1), or any combination thereof.

69. A method according to claim 68, wherein the vascular endothelial growth factor receptor (VEGFR) comprises FLT1, FLK1, Tie1, Tie2, or any combination thereof.

70. A method according to claim 47, wherein the ligand is an antibody to marker integrin αvβ3, a variant of antibody to integrin αvβ3m or any combination thereof.

71. A method according to claim 70, wherein the variant of antibody to marker integrin αvβ3 is Ber EP4, LM609, 2C3, or any combination thereof.

72. A method according to claim 47, wherein the ligand is an antibody to marker prostate specific membrane antigen, a variant of antibody to marker prostate specific membrane antigen, or any combination thereof.

73. A method according to claim 72, wherein the variant of antibody to marker prostate specific membrane antigen is MDX-070, 7E11-C5.3, or any combination thereof.

74. A method according to claim 46, wherein the marker adenovirus-cell surface receptor comprises coxsackie adenovirus cell surface receptor (CAR).

75. A method according to claim 46, wherein the marker cell cycle regulator comprises cyclin A, cyclin D, cyclin E, cdc2, or any combination thereof.

76. A method according to claim 46, wherein the marker oncogene comprises ras.

77. A method according to claim 46, wherein the marker apoptosis related factor comprises Fas, FasL, or any combination thereof.

78. A method according to claim 46, wherein the marker protein tyrosine kinase comprises VSrc, C-Src, or any combination thereof.

79. A method according to claim 46, wherein the marker cancer cell signal mediator comprises PI3KC2.

80. A method according to claim 46, wherein the marker cyclase-C receptor comprises guanylyl cyclase-C (GC-C) receptor.

81. A method according to claim 46, wherein the marker platelet derived growth factor receptor (PDGFR) comprises PDGFR-alpha, PDGFR-beta, or any combination thereof.

82. A method according to claim 46, wherein the marker the cobalamin receptor comprises methionine synthase, L-methylmalonyl-CoA mutase, or an combination thereof.

83. A method according to claim 46, wherein the marker glioma channel comprises glioma chloride channel.

84. A method according to claim 46, wherein the marker brain-specific chondroitin sulphate proteoglycan comprises brain enriched hyaluronan binding (BEHAB) protein receptor.

85. A method according to claim 46, wherein the marker catenin comprises alpha catenin, beta catenin, gamma catenin, or any combination thereof.

86. A method according to claim 46, wherein the marker protein antigen comprises p27, p73, or any combination thereof.

87. A method according to claim 47, wherein the ligand is an antibody to marker human milk fat globule receptor (HMFGR), a variant of antibody to marker HMFGR, or any combination thereof.

88. A method according to claim 87, wherein the variant of antibody to marker HMFGR is NCL-HMFG1, NCL-HMFG2, or any combination thereof.

89. A method according to claim 45, wherein the target associated with a disease of the subject's vascular system comprises a marker, and wherein the marker is an antigen associated with an apolipoprotein, lipoprotein, a vascular endothelial growth the for receptor (VEGFR), basic fibroblast growth factor receptor (bFGFR) or any combination thereof.

90. A method according to claim 89, wherein the marker lipoprotein comprises oxidized low density lipoprotein (Ox-LDL), malondialdehyde-modified LDL (MDA-LDL), or any combination thereof.

91. A method according to claim 90, wherein the ligand is antibody to marker OxLDL, a variant of antibody to marker OxLDL, or any combination thereof.

92. A method according to claim 91, wherein the variant of antibody to marker OxLDL is MDA-2.

93. A method according to claim 90, wherein the ligand is an antibody to marker MDA-LDL, a variant of antibody to marker MDA-LDL, or any combination thereof.

94. A method according to claim 93, wherein the variant of antibody to marker MDA-LDL is IK17.

95. A method according to claim 45, wherein the target associated with disease causing pathogen target is a virus, and wherein the virus is associated with tuberculosis.

96. A method according to claim 95, wherein target associated with tuberculosis comprises a marker, and wherein the marker is an antigen associated with APA.

97. A method according to claim 45, wherein, the target associated with disease causing pathogen is a virus, and wherein the virus is associated with human immunodeficiency virus (HIV).

98. A method according to claim 97, wherein the target comprises a marker, and wherein the, marker is T growth factor receptor alpha (TGFR-A) antigen associated with an HIV infected cell.

99. A method according to claim 45, wherein the target associated with disease causing pathogen target is a protozoan parasite, and wherein the protozoan parasite is associated with malaria.

100. A method according to claim 45, wherein the target associated with a central nervous system disease is multiple sclerosis and wherein the target comprises a marker, and wherein the marker is an $\alpha_4$-subunit of $\alpha_4\beta_1$-integrin (VLA-4), an $\alpha_4\beta_7$-integrin, or any combination thereof.

101. A method according to claim 99, wherein the target associated with disease causing pathogen comprises a marker, and wherein the marker is an apical membrane antigen-1 (AMA-1) on *Plasmodium falciparum*.

102. A method according to claim 45, wherein the target associated with non-cancerous disease material comprises a marker, and wherein the marker comprises a non-cancerous disease deposit, a non-cancerous disease precursor deposit, or any combination thereof.

103. A method according to claim 45, wherein the target associated with non-cancerous disease material is a vascular endothelial growth factor receptor associated with autoimmune joint degradation.

* * * * *